US011873330B2

(12) United States Patent
Bhakta et al.

(10) Patent No.: US 11,873,330 B2
(45) Date of Patent: Jan. 16, 2024

(54) CYSTEINE ENGINEERED ANTIBODIES AND CONJUGATES

(71) Applicant: Genentech, Inc.

(72) Inventors: Sunil Bhakta, San Ramon, CA (US); Jagath R. Junutula, Fremont, CA (US)

(73) Assignee: Genentech, Inc., South San Francisco, CA (US)

( * ) Notice: Subject to any disclaimer, the term of this patent is extended or adjusted under 35 U.S.C. 154(b) by 582 days.

(21) Appl. No.: 16/787,280

(22) Filed: Feb. 11, 2020

(65) Prior Publication Data

US 2020/0339664 A1    Oct. 29, 2020

Related U.S. Application Data

(60) Division of application No. 15/357,545, filed on Nov. 21, 2016, now Pat. No. 10,604,557, which is a division of application No. 14/185,080, filed on Feb. 20, 2014, now abandoned, which is a continuation of application No. 13/154,672, filed on Jun. 7, 2011, now Pat. No. 9,000,130.

(60) Provisional application No. 61/352,728, filed on Jun. 8, 2010.

(51) Int. Cl.
| | | |
|---|---|---|
| C07K 16/00 | (2006.01) | |
| C07K 16/32 | (2006.01) | |
| A61K 51/10 | (2006.01) | |
| A61K 47/68 | (2017.01) | |
| C07K 16/30 | (2006.01) | |

(52) U.S. Cl.
CPC .......... *C07K 16/00* (2013.01); *A61K 47/6801* (2017.08); *A61K 47/6803* (2017.08); *A61K 47/6811* (2017.08); *A61K 47/6817* (2017.08); *A61K 47/6829* (2017.08); *A61K 47/6851* (2017.08); *A61K 47/6855* (2017.08); *A61K 47/6889* (2017.08); *A61K 51/1051* (2013.01); *C07K 16/3092* (2013.01); *C07K 16/32* (2013.01); *A61K 47/6819* (2017.08); *C07K 2317/52* (2013.01); *C07K 2317/55* (2013.01); *C07K 2319/31* (2013.01)

(58) Field of Classification Search
CPC .... C07K 16/00; C07K 16/32; A61K 47/6803; A61K 47/6851; A61K 47/6889; A61K 47/6819
USPC ...................................................... 424/143.1
See application file for complete search history.

(56) References Cited

U.S. PATENT DOCUMENTS

| | | | |
|---|---|---|---|
| 5,219,996 A | 6/1993 | Bodmer et al. | |
| 6,248,564 B1 | 6/2001 | Walter et al. | |
| 6,737,056 B1 | 5/2004 | Presta | |
| 6,753,165 B1 | 6/2004 | Cox et al. | |
| 7,097,840 B2 | 8/2006 | Erickson et al. | |
| 7,276,585 B2 | 10/2007 | Lazar et al. | |
| 7,332,581 B2 | 2/2008 | Presta | |
| 7,442,778 B2 | 10/2008 | Gegg et al. | |
| 7,521,541 B2 | 4/2009 | Eigenbrot et al. | |
| 7,723,485 B2 | 5/2010 | Junutula et al. | |
| 7,776,814 B2 | 8/2010 | Domling | |
| 7,855,275 B2 | 12/2010 | Eigenbrot et al. | |
| 8,309,300 B2 | 11/2012 | Junutula et al. | |
| 8,394,922 B2 | 3/2013 | Eigenbrot | |
| 8,507,654 B2 | 8/2013 | Baker et al. | |
| 9,000,130 B2 | 4/2015 | Bhakta et al. | |
| 9,095,537 B2 | 8/2015 | Leclerc et al. | |
| 9,518,118 B2 | 12/2016 | Chen et al. | |
| 10,017,577 B2 | 7/2018 | Polakis et al. | |
| 10,179,820 B2 | 1/2019 | Chen et al. | |
| 2003/0021790 A1 | 1/2003 | Hsei et al. | |
| 2004/0005324 A1 | 1/2004 | Pilkington et al. | |
| 2004/0229310 A1 | 11/2004 | Simmons | |
| 2004/0235068 A1 | 11/2004 | Levinson | |
| 2005/0048572 A1 | 3/2005 | Reilly et al. | |
| 2007/0269369 A1 | 11/2007 | Gegg et al. | |
| 2008/0050310 A1 | 2/2008 | Ebens et al. | |
| 2008/0247951 A1 | 10/2008 | Koch et al. | |
| 2008/0305044 A1 | 12/2008 | McDonagh et al. | |
| 2008/0311134 A1 | 12/2008 | Junutula et al. | |
| 2009/0028856 A1 | 1/2009 | Chen et al. | |
| 2009/0068202 A1 | 3/2009 | Chen et al. | |
| 2009/0117100 A1 | 5/2009 | Mao et al. | |
| 2009/0258420 A1 | 10/2009 | van Vlijmen et al. | |

(Continued)

FOREIGN PATENT DOCUMENTS

| | | |
|---|---|---|
| CN | 101037475 A | 9/2007 |
| CN | 101065151 | 10/2007 |

(Continued)

OTHER PUBLICATIONS

Aerts et al., "Disparity between in vivo EGFR expression and 89Zr-labeled cetuximab uptake assessed with PET" J Nucl Med 50:123-131 (2009).

(Continued)

*Primary Examiner* — Yan Xiao

(74) *Attorney, Agent, or Firm* — McNeill Baur PLLC

(57) ABSTRACT

Cysteine engineered antibodies comprising a free cysteine amino acid in the heavy chain or light chain are prepared by mutagenizing a nucleic acid sequence of a parent antibody and replacing one or more amino acid residues by cysteine to encode the cysteine engineered antibody; expressing the cysteine engineered antibody; and isolating the cysteine engineered antibody. Certain highly reactive cysteine engineered antibodies were identified by the PHESELECTOR assay. Isolated cysteine engineered antibodies may be covalently attached to a capture label, a detection label, a drug moiety, or a solid support.

5 Claims, 12 Drawing Sheets

Specification includes a Sequence Listing.

(56) References Cited

U.S. PATENT DOCUMENTS

| | | |
|---|---|---|
| 2010/0003766 A1 | 1/2010 | Eigenbrot et al. |
| 2010/0028354 A1 | 2/2010 | McKinnon et al. |
| 2010/0111856 A1 | 5/2010 | Gill et al. |
| 2010/0158909 A1 | 6/2010 | McDonagh et al. |
| 2011/0033378 A1 | 2/2011 | Dimasi et al. |
| 2011/0137017 A1 | 6/2011 | Eigenbrot et al. |
| 2011/0301334 A1 | 12/2011 | Bhakta et al. |
| 2012/0148580 A1 | 6/2012 | Chennamsetty et al. |
| 2012/0213705 A1 | 8/2012 | Dimasi et al. |
| 2013/0066054 A1 | 3/2013 | Humphreys et al. |
| 2014/0288280 A1 | 9/2014 | Bhakta et al. |
| 2015/0017094 A1 | 1/2015 | Gill et al. |
| 2015/0017188 A1 | 1/2015 | Eigenbrot et al. |
| 2015/0165063 A1 | 6/2015 | Flygare et al. |
| 2015/0209445 A1 | 7/2015 | Maderna et al. |
| 2017/0174782 A1 | 6/2017 | Chen et al. |
| 2018/0185486 A1 | 7/2018 | Dragovich et al. |

FOREIGN PATENT DOCUMENTS

| | | |
|---|---|---|
| RU | 2006147264 A | 7/2020 |
| WO | 1989/01974 A1 | 3/1989 |
| WO | 1994/06474 | 3/1994 |
| WO | 2003/060080 A2 | 7/2003 |
| WO | 2004/010957 A2 | 2/2004 |
| WO | 2004/050849 A2 | 6/2004 |
| WO | 2005/117986 | 12/2005 |
| WO | 2006/034488 A2 | 3/2006 |
| WO | 2008/038024 | 4/2008 |
| WO | 2008/141044 A2 | 11/2008 |
| WO | 2009/052249 A1 | 4/2009 |
| WO | 2010/009391 A1 | 1/2010 |
| WO | 2010/108937 A2 | 9/2010 |
| WO | 2011/056983 | 5/2011 |
| WO | 2011/061492 A2 | 5/2011 |
| WO | 2011/156328 | 12/2011 |
| WO | 2012/009621 A1 | 1/2012 |
| WO | 2012/074757 A1 | 6/2012 |
| WO | 2013/093809 A1 | 6/2013 |
| WO | 2014/011518 A1 | 1/2014 |
| WO | 2014/022679 A2 | 2/2014 |
| WO | 2015/110935 A1 | 7/2015 |
| WO | 2016/040684 A1 | 3/2016 |
| WO | 2003/049704 A2 | 6/2019 |

OTHER PUBLICATIONS

All drugs online. Retrieved from the internet at www.all-drugs-online.com/Drugs/Oncology/1377.aspx, retrieved on Jan. 5, 2009.
Baca et al., "Antibody humanization using monovalent phage display" J Biol Chem 272(16):10678-10684 (1997).
Bernhard et al., "Cysteine analogs of recombinant barley ribosome inactivating protein form antibody conjugates with enhanced stability and potency in vitro" Bioconjug Chem 5:126-132 (1994).
Better et al., "Gelonin analogs with engineered cysteine residues form antibody immunoconjugates with unique properties" J Biol Chem 269(13):9644-9650 (Apr. 1, 1994).
Bhakta et al., "Engineering THIOMABs for Site Specific Conjugation of Thiol-Reactive Linkers," Antibody-Drug Conjugates Humana Press Inc.; Methods in Molecular Biology, pp. 189-203 (2013).
Biopharma. Retrieved from the Internet >URL: http://www.biopharma.com/Samples/184.html> Retrieved on Jan. 5, 2009.
Borjesson et al., "Performance of immuno-positron emission tomography with zirconium-89-labeled chimeric monoclonal antibody U36 in the detection of lymph node metastases in head and neck cancer patients" Clin Cancer Res 12(7):2133-2140 (2006).
Boswell et al., "Impact of Drug Conjugation on Pharmacokinetics and Tissue Distribution of Anti-STEAP1 Antibody-Drug Conjugates in Rats," Bioconjugate Chemistry 22(10): 1994-2004 (2011).
Carter et al., "Humanization of an Anti-p185HER Antibody for Human Cancer Therapy" P Natl Acad Sci USA 89(10):4285-4289 (May 1992).
CellTiter-Glo Luminescent Cell Viability Assay (Technical Bulletin No. 288), Madison, WI:Promega Corp., pp. 1-11 (Feb. 2004).
Chang et al., "High-Level Secretion of Human Growth Hormone by *Escherichia coli*" Gene 55:189-196 (1987).
Chen et al., "Charge-based analysis of antibodies with engineered cysteines from multiple peaks to a single main peak" mAbs 1(6):563-571 (Nov./Dec. 2009).
Chmura et al., "Antibodies with infinite affinity" P Natl Acad Sci USA 98(15):8480-8484. (Jul. 17, 2001).
Collaborative Computational Project, No. 4, "The CCP4 Suite: Programs for Protein Crystallography" Acta Cryst D50:760-763 (1994).
Corneillie et al., "Converting Weak Binders into Infinite Binders" Bioconjugate Chem 15(6):1389-1391 (2004).
Dennis et al., "Albumin binding as a general strategy for improving the pharmacokinetics of proteins" J Biol Chem 277(38):35035-35043 (Sep. 20, 2002).
Dijkers et al., "Development and characterization of clinical-grade 89Zr-Trastuzumab for HER2/neu ImmunoPET imaging" J Nucl Med 50(6):974-981 (Jun. 2009).
Doronina et al., "Development of potent monoclonal antibody auristatin conjugates for cancer therapy" Nat Biotechnol 21(7):778-784 (Jul. 2003).
Eigenbrot et al., "X-Ray structures of the antigen-binding domains from three variants of humanized anti-p185HER2 antibody 4D5 and comparison with molecular modeling" J Mol Biol 229:969-995 (1993).
Gagnon et al., "High-throughput in vivo Screening of Targeted Molecular Imaging Agents" P Natl Acad Sci USA 106(42):17904-17909 (Oct. 2009).
Gerstner et al., "Sequence Plasticity in the Antigen-binding Site of a Therapeutic Anti-HER2 Antibody" J Mol Biol 321:851-862 (2002).
Gill et al., "A Modular Platform for the Rapid Site-Specific Radiolabeling of Proteins with 18F Exemplified by Quantitative Positron Emission Tomography of Human Epidermal Growth Factor Receptor 2" J Med Chem 52:5816-5825 (2009).
Gomez et al., "Triple Light Chain Antibodies: Factors That Influence Its Formation in Cell Culture" Biotechnology and Bioengineering 105(4):748-760 (Mar. 1, 2010).
Govindan et al., "Deferoxamine as a chelator for 67 Ga in the preparation of antibody conjugates" Nucl Med Biol 32:513-519 (Apr. 14, 2005).
Greenwood et al., "Engineering multiple-domain forms of the therapeutic antibody CAMPATH-1H: effects on complement lysis" Therapeutic Immunology 1(5):247-255 (Oct. 1994).
Hafner et al., "Noncompetitive Immunoassay of Small Analytes at the Femtomolar Level by Affinity Probe Capillary Electrophoresis: Direct Analysis of Digoxin Using a Uniform-Labeled scFv Immunoreagent" Anal Chem 72(23):5779-5786 (Dec. 1, 2000).
Hausner et al., "Use of a peptide derived from foot- and-mouth disease virus for the noninvasive imaging of human cancer: generation and evaluation of 4-[18F]fluorobenzoyl A20FMDV2 for in vivo imaging of integrin alphavbeta6 expression with positron emission tomography," Cancer Res 67(16):7833-7840 (Aug. 2007).
Hausner et al., "In vivo positron emission tomography (PET) imaging with an alphavbeta6 specific peptide radiolabeled using 18F-'click' chemistry: evaluation and comparison with the corresponding 4-[18F]fluorobenzoyl- and 2-[18F]fluoropropionyl-peptides" J Med Chem. 51(19):5901-4 (2008).
Hausner et al., "Targeted In vivo Imaging of Integrin Alphavbeta6 with an Improved Radiotracer and Its Relevance in a Pancreatic Tumor Model" Cancer Res 69(14):5843-5850 (Jul. 2009).
Ho et al., "Site-Directed Mutagenesis by Overlap Extension Using the Polymerase Chain Reaction" Gene 77(1):51-59 (1989).
International Search Report and Written Opinion for PCT/US2015/049771 dated Mar. 15, 2016, 25 pages.
International Search Report for PCT/US2010/055465, dated Jan. 24, 2011, 6 pages.
International Search Report for PCT/US2011/039386 dated Nov. 2, 2011, 5 pages.

(56) References Cited

OTHER PUBLICATIONS

Ito et al., "A general method for introducing a series of mutations into cloned DNA using the polymerase chain reaction" Gene 102(1):67-70 (Jun. 15, 1991).
Junutula et al., "ThioMabs: improving safety abd retaining efficacy of antibody drug conjugates." Proceedings of the Annual Meeting, American Association for Cancer Research 48: 220-221 (2007).
Junutula et al., "Engineered Thio-Trastuzumab-DM1 Conjugate with an Improved Therapeutic Index to Target Human Epidermal Growth Factor Receptor 2-Positive Breast Cancer" Clinical Cancer No Research 16:4769-4778 (Aug. 30, 2010).
Junutula et al., "Rapid identification of reactive cysteine residues for site-specific labeling of antibody-Fabs" J Immunol Methods 332:41-52 (2008).
Junutula et al., "Site-specific conjugation of a cytotoxic drug to an antibody improves the therapeutic index" Nat Biotechnol 26(8):925-32 (Aug. 2008).
Kabat et al. US Department of Health and Human Services, Public Health Service, NIH 4th edition,:160 and 294 ( 1987).
Kanno et al., "Assembling of engineered IgG-binding protein on gold surface for highly oriented antibody immobilization" J Biotechnol 76(2-3):207-214 (Jan. 21, 2000).
King et al., "Facile synthesis of maleimide bifunctional linkers" Tetrahedron Lett 43:1987-1990 (2002).
Kumaresan et al., "Evaluation of Ketone-Oxime Method for Developing Therapeutic On-Demand Cleavable Imrnunoconjugates" Bioconjugate Chem 19:1313-1318 (2008).
Lambert, "Drug-conjugated monoclonal antibodies for the treatment of cancer" Curr Opin Pharmacol 5(5):543-549 (Oct. 2005).
Lewis et al., "Maleimidocysteineamido-DOTA derivatives: new reagents for radiometal chelate conjugation to antibody sulfhydryl groups undergo pH-dependent cleavage reactions" Bioconjug Chem 9(1):72-86 (Jan. 1998).
Liu, "Bifunctional coupling agents for radiolabeling of biomolecules and target-specific delivery of metallic radionuclides" Adv Drug Deliver Rev 60:1347-1370 (2008).
Lowman, "Phage display of peptide libraries on protein scaffolds" Methods Molecular Biology 87:249-264 (1998).
Lund et al., "Expression and characterization of truncated forms of humanized L243 IgG1. Architectural features can influence synthesis of its oligosaccharide chains and affect superoxide production triggered through human Fcγ receptor I" Eur J Biochem 267:7246-7256 (2000).
Lyons et al., "Site-specific attachment to recombinant antibodies via introduced surface cysteine residues" Protein Engineering 3(8):703-708 (1990).
MacCallum et al., "Antibody-antigen interactions: contact analysis and binding site topography" J Mol Biol 262:732-745 (1996).
Meijs et al., "A facile method for the labeling of proteins with zirconium Isotopes" Nucl Med Biol 23:439-448 (1996).
Meijs et al., "Zirconium-labeled monoclonal antibodies and their distribution in tumor-bearing nude mice" J Nucl Med 38(1):112-118 (Jan. 1997).
Miller, "Syntheses and therapeutic potential of hydroxamic acid based siderophores and analogues" Chem Rev 89:1563-1579 (1989).
Nagengast et al., "In vivo VEGF imaging with radiolabled bevacizumab in a human ovarian tumor xenograft" J Nucl Med 48:1313-1319 (2007).
Olafsen et al., "Characterization of engineered anti-p185HER-2 (scFv-CH3)2 antibody fragments (minibodies) for tumor targeting," Protein Eng Des Sel 17(4):315-323 (2004).
Panowski et al., "Site-specific antibody drug conjugates for cancer therapy," mAbs 6(1): 34-45 (2014).
Payne, "Progress in Immunoconjugate Cancer Therapeutics" Cancer Cell 3:207-212 (2003).
Perk et al., "(89)Zr as a PET surrogate radioisotope for scouting biodistribution of the therapeutic radiometals (90)Y and (177)Lu in tumor-bearing nude mice after coupling to the internalizing antibody cetuximab," J Nucl Med 46(11):1898-1906 (Nov. 2005).
Perk et al., "Preparation and evaluation of (89)Zr-Zevalin for monitoring of (90)Y-Zevalin biodistribution with positron emission tomography," Eur J Nucl Med Mol Imaging 33:1337-1345 ( 2006).
Perk et al., "Quantitative PET imaging of Met-expressing human cancer xenografts with 89Zr-labelled monoclonal antibody DN30," Eur J Nucl Med Mol Imaging 35:1857-1867 (2008).
Renard et al., "Deriving Topological Constraints from Functional Data for the Design of Reagentless Fluorescent Immunosensors" J Mol Biol 326:167-175 (2003).
Roitt et al., Roitt's Essential Immunology, 110-111 (2000).
Roitt et al., Roitt's Essential Immunology, 110-111 (2000), English translation (4 pages).
Roux et al., "Comparisons of the ability of human IgG3 hinge mutants, IgM, IgE, and IgA2, to form small immune complexes: a role for flexibility and geometry" J Immunol 161:4083-4090 (1998).
Rudikoff et al., "Single amino acid substitution altering antigen-binding specificity" P Natl Acad Sci USA 79:1979-1983 (Mar. 1982).
Schelte et al., "Differential Reactivity of Maleimide and Bromoacetyl Functions with Thiols: Application to the Preparation of Liposomal Diepitope Constructs" Bioconjugate Chem 11:118-123 (2000).
Senter, "Immunoconjugates comprised of drugs with impaired cellular permeability: a new approach to targeted therapy, Abstract No. 623" Proceedings of the American Association for Cancer Research, (2004).
Shen et al., "Conjugation site modulates the in vivo stability and therapeutic activity of antibody-drug conjugates" Nature Biotechnology 30(2):184-190 (Feb. 2012).
Shopes, "A Genetically Engineered Human IgG with Limited Flexibility Fully Initiates Cytolysis Via Complement" Mol Immunol 30(6):603-609 (1993).
Singh et al., "Labeling of antibodies by in situ modification of thiol groups generated from selenol-catalyzed reduction of native disulfide bonds" Anal Biochem 304(2):147-156 (May 15, 2002).
Stimmel et al., "Site-specific Conjugation on Serine—Cysteine Variant Monoclonal Antibodies" J Biol Chem 275(39):30445-50 (Sep. 29, 2000).
Sukumaran et al., "Mechanism-Based Pharmacokinetic/ Pharmacodynamic Model for THIOMAV™ Drug Conjug," Pharmaceutical Research 32(6): 1884-1893 (2015).
Sun et al., "Enabling ScFvs as multi-drug carriers: a dendritic approach" Bioorg Med Chem 11:1761-1768 (2003).
Sun et al., "Syntheses of dendritie linkers containing chlorambucil residues for the preparation of antibody-multidrug immunoconjugates" Bioorg Med Chem Lett 12:2213-2215 (2002).
Tartis et al., "Dynamic MicroPET Imaging of Ultrasound Contrast Agents and Lipid Delivery" J Control Release 131:160-166 (2008).
Tinianow et al., "Site-specifically 89Zr-labeled Monoclonal Antibodies for ImmunoPET" Nucl Med Biol 37:289-297 (2010).
Trail et al., "Monoclonal Antibody Drug Immunoconjugates for Targeted Treatment of Cancer" Cancer Immunol Immunother 52:328-337 (2003).
Tu et al., "Protein footprinting at cysteines: probing ATP-modulated contacts in cysteine-substitution mutants of yeast DNA topoisomerase II" P Natl Acad Sci Usa 96(9):4862-4867 (Apr. 27, 1999).
Verel et al., "Quantitative 89Zr immuno-PET for in vivo scouting of 90Y-labeled monoclonal antibodies in xenograft-bearing nude mice," J Nucl Med 44:1663-1670 (2003).
Verel et al., "89Zr immuno-PET: comprehensive procedures for the production of 89Zr-labeled monoclonal antibodies," J Nucl Med 44(8):1271-1281 (Aug. 2003).
Vosjan et al., "Conjugation and Radiolabeling of Monoclonal Antibidies with Zirconium-89 for PET Imaging Using the Bifunctional Chelate p-isothiocyanatobenzyl-desferrioxamine" Nat Protoc 5(4):739-743 (2010).
Voynov et al., "Design and application of antibody cysteine variants" Bioconjug Chem 21(2):385-392 (Feb. 2010).
Wu et al., "Arming antibodies: prospects and challenges for immunoconjugates" Nat Biotechnol 23(9):1137-1146 (Sep. 23, 2005).
Wu et al., "Humanization of a Murine Monoclonal Antibody by Simultaneous Optimization of Framework and CDR Residues" J Mol Biol 294:151-162 (1999).

(56) References Cited

OTHER PUBLICATIONS

Xu et al., "Characterization of intact antibody-drug conjugates from plasma/serum in vivo by affinity capture capillary liquid chromatography-mass spectrometry" Analytical Biochemistry 412:56-66 (2011).
Yasuhisa et al., "Identification of Highly Reactive Cysteine Residues at Less Exposed Positions in the Fab Constant Region for Site-specific Conjugation," Bioconjugate Chemistry, 10.1021 (May 2015).
Zhang et al., "Complete disulfide bond assignment of a recombinant immunoglobulin G4 monoclonal antibody" Anal Biochem 311(1):1-9 (Dec. 1, 2002).

```
Sequential Numbering
                   10        20        30
4d5v7fabH   EVQLVESGGGLVQPGGSLRLSCAASGFNIKDTYIHW
            ***********************************
4d5v7fabH   EVQLVESGGGLVQPGGSLRLSCAASGFNIKDTYIHW
                   10        20        30
Kabat Numbering 40        50        60        70        80
4d5v7fabH   VRQAPGKGLEWVARIYPTNGYTRYADSVKGRFTISADTSKNTAYLQMNSL
            **************************************************
4d5v7fabH   VRQAPGKGLEWVARIYPTNGYTRYADSVKGRFTISADTSKNTAYLQMNSL
              40        50   a    60        70        80   abc 90       100       110       120       130
4d5v7fabH   RAEDTAVYYCSRWGGDGFYAMDYWGQGTLVTVSSASTKGPSVFPLAPSSK
            **************************************************
4d5v7fabH   RAEDTAVYYCSRWGGDGFYAMDYWGQGTLVTVSSASTKGPSVFPLAPSSK
                  90       100abc     110       120

140       150       160       170       180
4d5v7fabH   STSGGTAALGCLVKDYFPEPVTVSWNSGALTSGVHTFPAVLQSSGLYSLS
            **************************************************
4d5v7fabH   STSGGTAALGCLVKDYFPEPVTVSWNSGALTSGVHTFPAVLQSSGLYSLS
              130       140       150       160       170

190       200       210       220
4d5v7fabH   SVVTVPSSSLGTQTYICNVNHKPSNTKVDKKVEPKSC
            *************************************
4d5v7fabH   SVVTVPSSSLGTQTYICNVNHKPSNTKVDKKVEPKSC
              180       190       200       210
```

Figure 1B

CYSTEINE ENGINEERED ANTIBODIES AND CONJUGATES

REFERENCE TO RELATED APPLICATIONS

This application is a divisional U.S. patent application Ser. No. 15/357,545, filed Nov. 21, 2016, which is a divisional of U.S. patent application Ser. No. 14/185,080, filed Feb. 20, 2014, which is a continuation of U.S. patent application Ser. No. 13/154,672, filed Jun. 7, 2011, now U.S. Pat. No. 9,000,130 B2, which claims the benefit under 35 USC § 119(e) of U.S. Provisional Application No. 61/352,728, filed Jun. 8, 2010, each of which is incorporated by reference herein in its entirety for any purpose.

FIELD OF THE INVENTION

The invention relates generally to antibodies engineered with reactive cysteine residues and more specifically to antibodies with therapeutic or diagnostic applications. The cysteine engineered antibodies may be conjugated with chemotherapeutic drugs, toxins, affinity ligands such as biotin, and detection labels such as fluorophores. The invention also relates to methods of using antibodies and antibody-drug conjugate compounds for in vitro, in situ, and in vivo diagnosis or treatment of mammalian cells, or associated pathological conditions.

BACKGROUND OF THE INVENTION

Antibody drug conjugates (ADC) are attractive targeted chemo-therapeutic molecules as they combine ideal properties of both antibodies and cytotoxic drugs by targeting potent cytotoxic drugs to the antigen-expressing tumor cells, thereby enhancing their anti-tumor activity. The successful ADC development for a given target antigen depends on optimization of antibody selection, linker stability, cytotoxic drug potency and mode of linker-drug conjugation to the antibody.

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods are inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multistep conjugation process may be nonreproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Antibody cysteine thiol groups are generally more reactive, i.e. more nucleophilic, towards electrophilic conjugation reagents than antibody amine or hydroxyl groups. Engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of E. coli, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or non-specific, by misfolding or loss of tertiary structure (Zhang et al (2002) Anal. Biochem. 311:1-9).

Antibodies with cysteine substitutions (ThioMabs) at sites where the engineered cysteines are available for conjugation but do not perturb immunoglobulin folding and assembly or alter antigen binding and effector functions (Junutula, et al., 2008b Nature Biotech., 26(8):925-932; Dornan et al (2009) Blood 114(13):2721-2729; U.S. Pat. Nos. 7,521,541; 7,723,485; WO2009/052249). These ThioMabs can then be conjugated to cytotoxic drugs through the engineered cysteine thiol groups to obtain ThioMab drug conjugates (TDC) with uniform stoichiometry (~2 drugs per antibody). Studies with multiple antibodies against different antigens have shown that TDC are as efficacious as conventional ADC in xenograft models and are tolerated at higher doses in relevant preclinical models. ThioMab drug conjugates have been engineered with drug attachment at different parts of the antibody (light chain-Fab, heavy chain-Fab and heavy chain-Fc). The in vitro & in vivo stability, efficacy and PK properties of TDC provide a unique advantage over conventional ADC due to their homogeneity and site-specific conjugation to cytotoxic drugs.

SUMMARY

The invention includes an isolated cysteine engineered antibody comprising a free cysteine amino acid in the heavy chain or light chain.

An aspect of the invention is a process to prepare the isolated cysteine engineered antibody by mutagenizing a nucleic acid sequence of a parent antibody by replacing one or more amino acid residues by cysteine to encode the cysteine engineered antibody; expressing the cysteine engineered antibody; and isolating the cysteine engineered antibody.

Another aspect of the invention is a conjugate of the isolated cysteine engineered antibody wherein the antibody is covalently attached to a capture label, a detection label, a drug moiety, or a solid support.

BRIEF DESCRIPTION OF THE DRAWINGS

FIG. 1B shows a sequential numbering scheme (top row), starting at the N-terminus in comparison with the Kabat numbering scheme (bottom row) for 4D5v7fabH. Kabat numbering insertions are noted by a,b,c.

DETAILED DESCRIPTION OF EXEMPLARY EMBODIMENTS

Figure 1A:
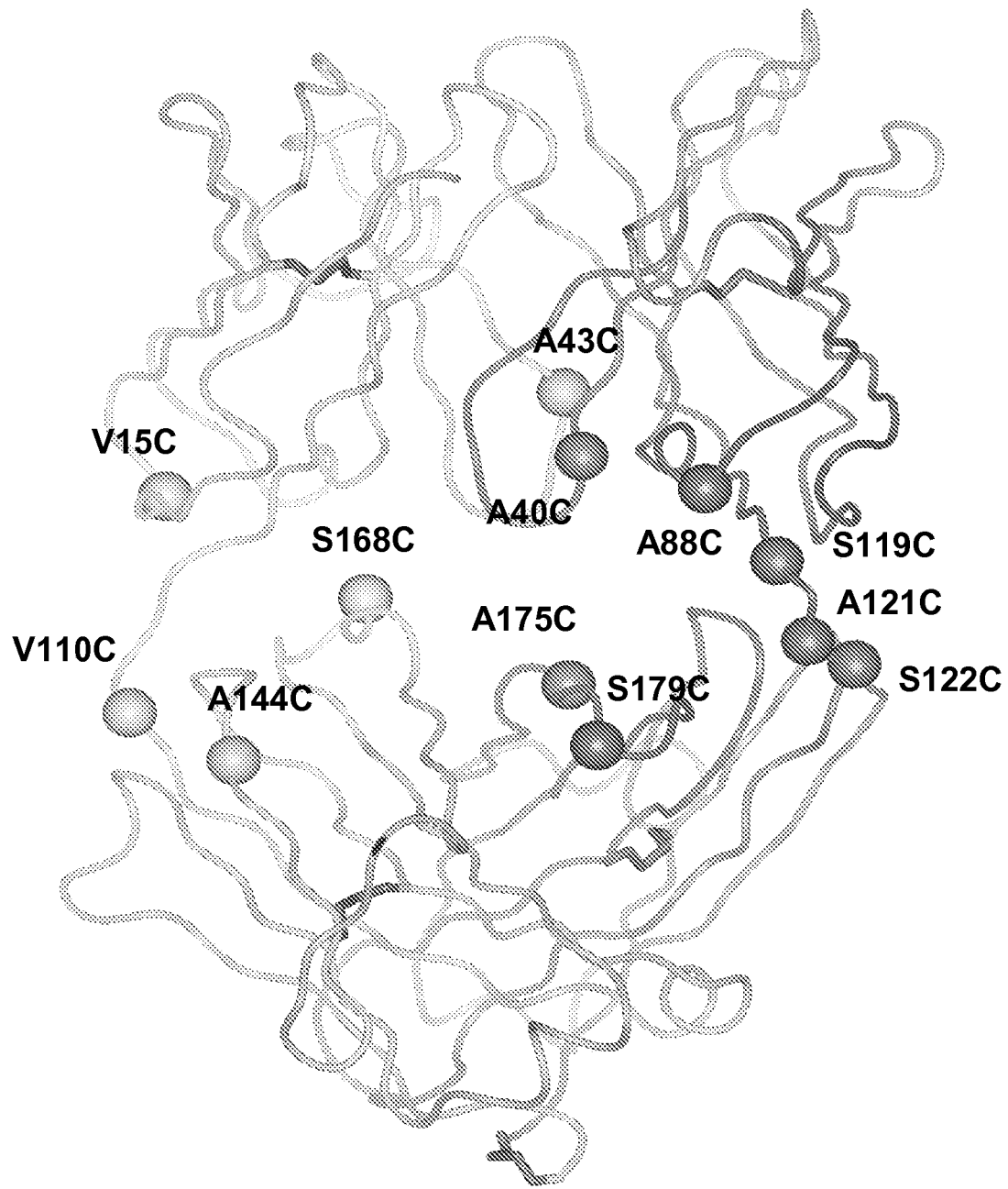
FIG. 1A shows a three-dimensional representation of the hu4D5Fabv7 antibody fragment derived by X-ray crystal coordinates. The structure positions of the exemplary engineered Cys residues of the heavy and light chains are numbered (according to a sequential numbering system).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310).

An "ErbB receptor" is a receptor protein tyrosine kinase which belongs to the ErbB receptor family whose members are important mediators of cell growth, differentiation and survival. The ErbB receptor family includes four distinct members including epidermal growth factor receptor (EGFR, ErbB1, HER1), HER2 (ErbB2 or p185neu), HER3 (ErbB3) and HER4 (ErbB4 or tyro2). A panel of anti-ErbB2 antibodies has been characterized using the human breast tumor cell line SKBR3 (Hudziak et al (1989) Mol. Cell. Biol. 9(3):1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α (U.S. Pat. No. 5,677,171). The anti-ErbB2 antibodies discussed in Hudziak et al. are further characterized in Fendly et al (1990) Cancer Research 50:1550-1558; Kotts et al. (1990) In Vitro 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2): 979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20):14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Preferably, the ErbB receptor is native sequence human ErbB receptor. Accordingly, a "member of the ErbB receptor family" includes EGFR (ErbB1), ErbB2, ErbB3, ErbB4.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native ErbB ligand or with at least one ligand binding domain of a native ErbB receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, DC 20559, on Dec. 10, 1991.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, MD). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the VH and VL domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). Anti-ErbB2 antibody scFv fragments are described in WO 93/16185; U.S. Pat. Nos. 5,571,894; and 5,587,458.

"Humanized" forms of non-human (e.g., rodent) antibodies are chimeric antibodies that contain minimal sequence derived from non-human immunoglobulin. Humanization is a method to transfer the murine antigen binding information to a non-immunogenic human antibody acceptor, and has resulted in many therapeutically useful drugs. The method of humanization generally begins by transferring all six murine complementarity determining regions (CDRs) onto a human antibody framework (Jones et al, (1986) Nature 321:522-

525). These CDR-grafted antibodies generally do not retain their original affinity for antigen binding, and in fact, affinity is often severely impaired. Besides the CDRs, select non-human antibody framework residues must also be incorporated to maintain proper CDR conformation (Chothia et al (1989) Nature 342:877). The transfer of key mouse framework residues to the human acceptor in order to support the structural conformation of the grafted CDRs has been shown to restore antigen binding and affinity (Riechmann et al (1992) J. Mol. Biol. 224, 487-499; Foote and Winter, (1992) J. Mol. Biol. 224:487-499; Presta et al (1993) J. Immunol. 151, 2623-2632; Werther et al (1996) J. Immunol. Methods 157:4986-4995; and Presta et al (2001) Thromb. Haemost. 85:379-389). For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see U.S. Pat. No. 6,407,213; Jones et al (1986) Nature, 321:522-525; Riechmann et al (1988) Nature 332:323-329; and Presta, (1992) Curr. Op. Struct. Biol., 2:593-596.

A "free cysteine amino acid" refers to a cysteine amino acid residue which has been engineered into a parent antibody, has a thiol functional group (—SH), and is not paired as an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of about 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

Exemplary parent antibodies include antibodies having affinity and selectivity for cell surface and transmembrane receptors and tumor-associated antigens (TAA).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (MA). Sometimes, the anti-ErbB2 antibody will not significantly cross-react with the rat neu protein, e.g., as described in Schecter et al. (1984) Nature 312:513 and Drebin et al (1984) Nature 312:545-548.

Molecular targets for antibodies encompassed by the present invention include CD proteins and their ligands, such as, but not limited to: (i) CD3, CD4, CD8, CD19, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and ∀v/∃3 integrin, including either alpha or beta subunits thereof (e.g. anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, 37 etc; and (v) cell surface and transmembrane tumor-associated antigens (TAA).

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (trastuzumab, HERCEPTIN®) as in U.S. Pat. No. 5,821,337.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer which "overexpresses" an antigenic receptor is one which has significantly higher levels of the receptor, such as ErbB2, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, or polymerase chain reaction (PCR) techniques, such as real time quantitative PCR (RT-PCR).

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins, typically through fusions to either pIII or pVIII of filamentous phage (Wells and Lowman, (1992) Curr. Opin. Struct. Biol., 3:355-362, and references cited therein). In monovalent phage display, a protein or peptide library is fused to a phage coat protein or a portion thereof, and expressed at low levels in the presence of wild type protein. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991). Phage display includes techniques for producing antibody-like molecules (Janeway, C., Travers, P., Walport, M., Shlomchik (2001) *Immunobiology*, 5th Ed., Garland Publishing, New York, p62'7-628; Lee et al).

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

"Linker", "Linker Unit", or "link" means a chemical moiety comprising a covalent bond or a chain of atoms that covalently attaches an antibody to a drug moiety. In various embodiments, a linker is specified as L. Linkers include a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

Cysteine Engineered Antibodies

The compounds of the invention include cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

The design, selection, and preparation methods of the invention enable cysteine engineered antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

The parent antibody may also be a humanized antibody selected from huMAb4D5-1, huMAb4D5-2, huMAb4D5-3, huMAb4D5-4, huMAb4D5-5, huMAb4D5-6, huMAb4D5-7 and huMAb4D5-8 (Trastuzumab, HERCEPTIN®) as described in Table 3 of U.S. Pat. No. 5,821,337, expressly incorporated herein by reference; humanized 520C9 (WO 93/21319) and humanized 2C4 antibodies as described herein.

Cysteine engineered antibodies of the invention may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

The sites identified on the exemplary antibody fragment, hu4D5Fabv8, herein are primarily in the constant domain of an antibody which is well conserved across all species of antibodies. These sites should be broadly applicable to other antibodies, without further need of structural design or knowledge of specific antibody structures, and without interference in the antigen binding properties inherent to the variable domains of the antibody.

Cysteine engineered antibodies which may be useful in the treatment of cancer include, but are not limited to, antibodies against cell surface receptors and tumor-associated antigens (TAA). Such antibodies may be used as naked antibodies (unconjugated to a drug or label moiety) or as Formula I antibody-drug conjugates (ADC). Tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4); NP 001194 bone morphogenetic protein receptor, type IB/pid=NP_001194.1. Cross-references: MIM:603248; NP_001194.1; AY065994

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO2002064798 (claim 33; Page 93-95); WO200014228 (claim 5; Page 133-136); US2003224454 (FIG. 3); WO2003025138 (claim 12; Page 150); NP_003477 solute carrier family 7 (cationic amino acid transporter, y+system), member 5/pid=NP_003477.3— Homo sapiens; Cross-references: MIM:600182; NP_003477.3; NM_015923; NM_003486_1

Figure 2A:
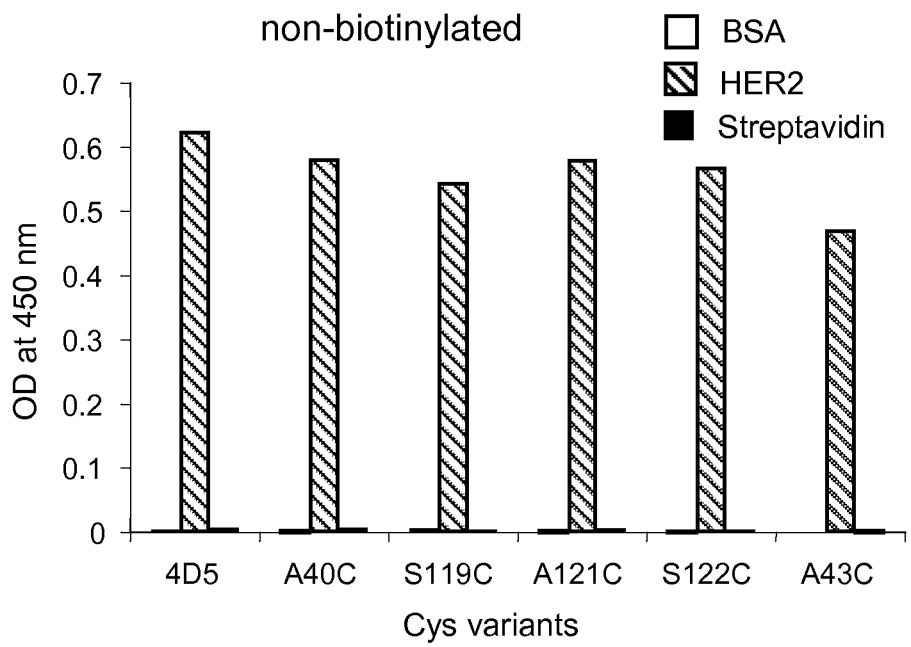
FIGS. 2A and 2B show binding measurements with detection of absorbance at 450 nm of hu4D5Fabv8 and hu4D5Fabv8 Cys mutant (ThioFab) phage variants: (A) non-biotinylated phage-hu4D5Fabv8 and (B) biotinylated phage-hu4D5Fabv8 (B) by the PHESELECTOR assay for interactions with BSA (open bar), HER2 (striped bar) or streptavidin (solid bar).

(3) STEAP1 (six transmembrane epithelial antigen of prostate, Genbank accession no. NM_012449); Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM: 604415; NP_036581.1; NM_012449_1

(4) 0772P (CA125, MUC16, Genbank accession no. AF361486); J. Biol. Chem. 276 (29):27371-27375 (2001)); WO2004045553 (claim 14); WO200292836 (claim 6; FIG. 12); WO200283866 (claim 15; Page 116-121);

US2003124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57); Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140); Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11); Accession: Q9P283; EMBL; AB040878; BAA95969.1. Genew; HGNC:10737

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1

Figure 6:
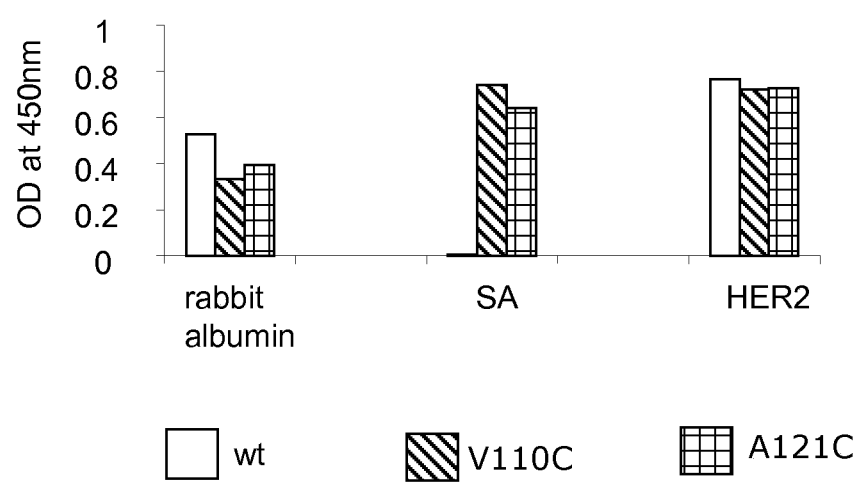
FIG. 6 shows ELISA analysis with detection of absorbance at 450 nm of biotinylated ABP-hu4D5Fabv8 wild type (wt), and ABP-hu4D5Fabv8 cysteine mutants V110C and A121C for binding with rabbit albumin, streptavidin (SA), and HER2.

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, sl-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004

(10) MSG783 (RNF124, hypothetical protein FLJ20315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6); Cross-references: LocusID:54894; NP_060233.2; NM_017763_1

Figure 4A:
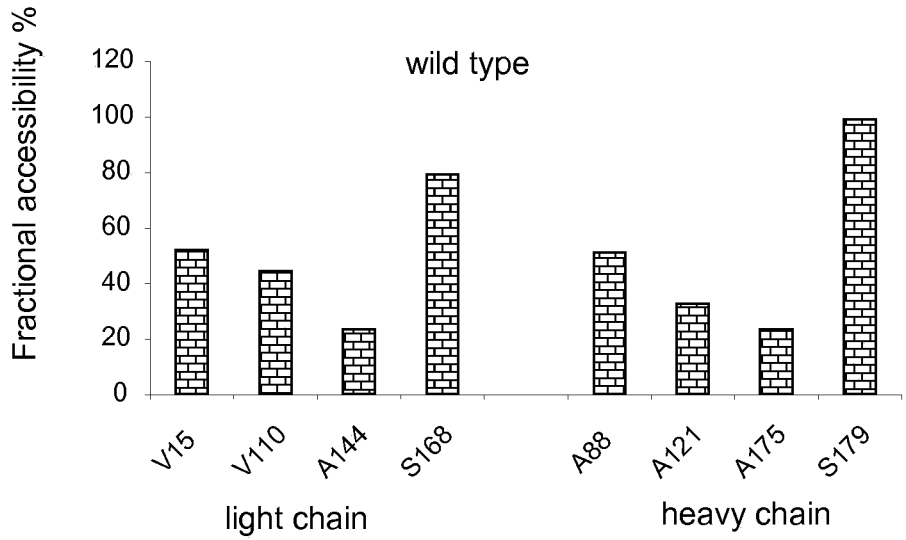
FIG. 4A shows Fractional Surface Accessibility values of residues on wild type hu4D5Fabv8. Light chain sites are on the left side and heavy chain sites are on the right side.
Figure 4B:
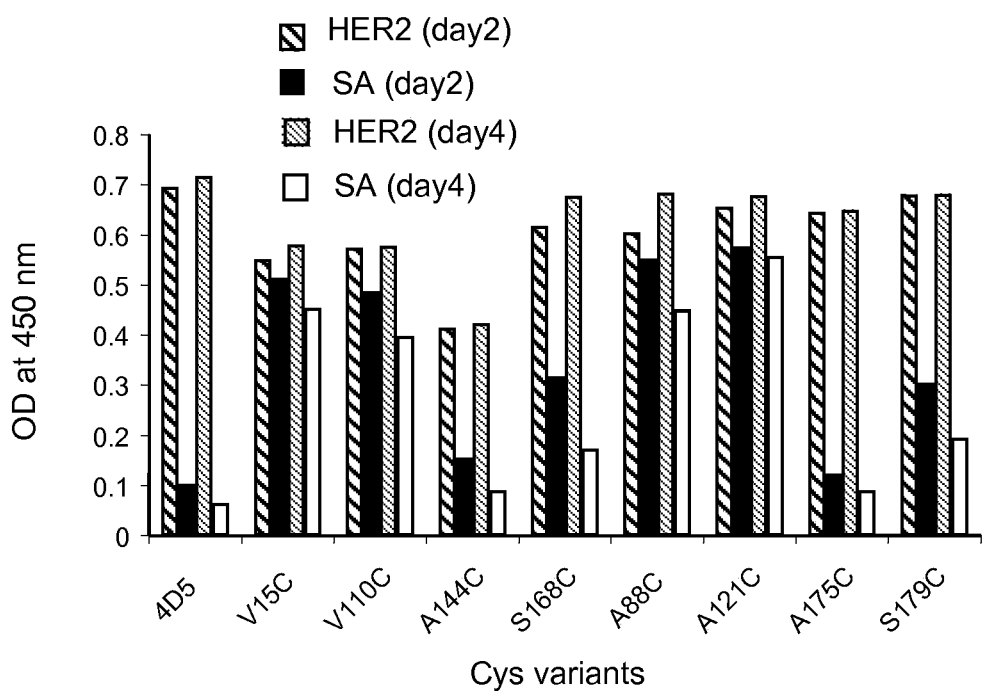
FIG. 4B shows binding measurements with detection of absorbance at 450 nm of biotinylated hu4D5Fabv8 (left) and hu4D5Fabv8 Cys mutant (ThioFab) variants for interactions with HER2 (day 2), streptavidin (SA) (day 2), HER2 (day 4), and SA (day 4). Phage-hu4D5Fabv8 Cys variants were isolated and stored at 4° C. Biotin conjugation was carried out either at day 2 or day 4 followed by PHESELECTOR analyses to monitor their interaction with Her2 and streptavidin as described in Example 2, and probe the stability of reactive thiol groups on engineered ThioFab variants.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10); Cross-references: GI:22655488; AAN04080.1; AF455138_1

Figure 9A:
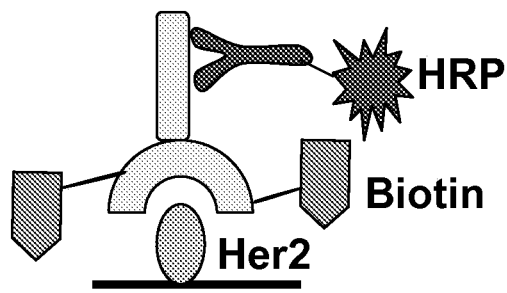
FIG. 9A shows a cartoon depiction of biotinylated antibody binding to immobilized HER2 with binding of HRP labeled secondary antibody for absorbance detection.

(12) TrpM4 (BR22450, FLJ20041, TRPM4, TRPM4B, transient receptor potential cation channel, subfamily M, member 4, Genbank accession no. NM_017636); Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212); Ciccodicola, A., et al EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

Figure 9B:
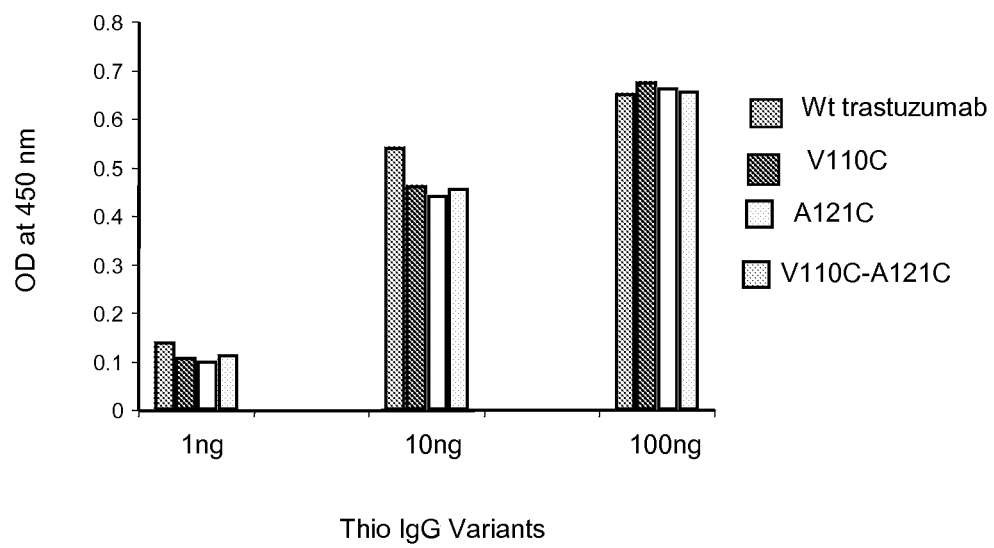
FIG. 9B shows binding measurements with detection of absorbance at 450 nm of biotin-maleimide conjugated thio-trastuzumab variants and non-biotinylated wild type trastuzumab in binding to immobilized HER2. From left to right: V110C (single cys), A121C (single cys), V110C/A121C (double cys), and trastuzumab. Each thio IgG variant and trastuzumab was tested at 1, 10, and 100 ng.

(14) CD21 ($CR_2$ (Complement receptor 2) or C3DR (C3d/Epstein Barr virus receptor) or Hs.73792 Genbank accession no. M26004); Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIGS. 9.1-9.9); WO2004020595 (claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674); Proc. Natl. Acad. Sci. U.S.A. (2003) 100

(7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130); Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12); WO2003089624 (claim 25); Cross-references: MIM:606509; NP_110391.2; NM_030764_1

Figure 7:
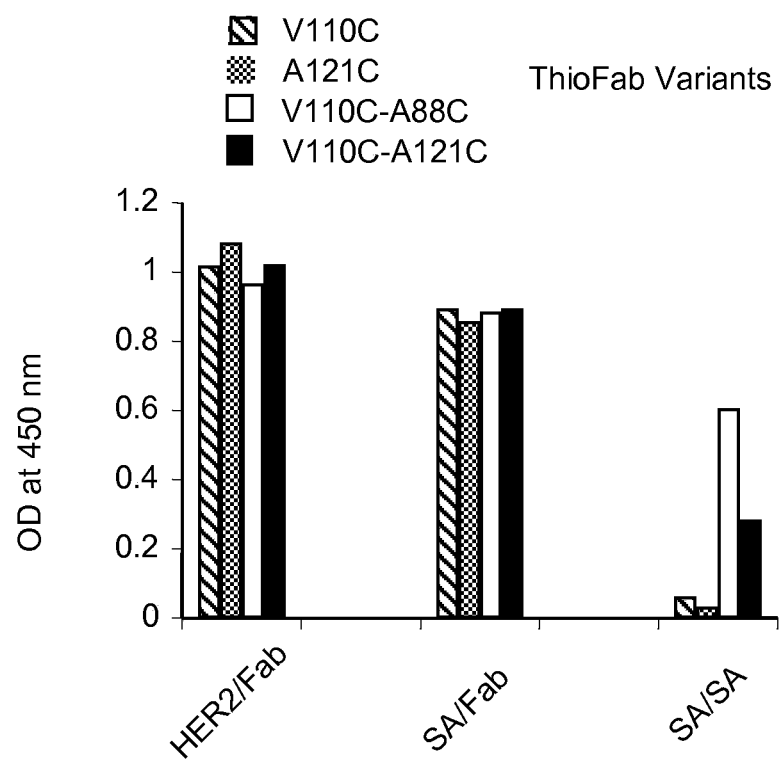
FIG. 7 shows ELISA analysis with detection of absorbance at 450 nm of biotinylated ABP-hu4D5Fabv8 cysteine mutants (ThioFab variants): (left to right) single Cys variants ABP-V110C, ABP-A121C, and double Cys variants ABP-V110C-A88C and ABP-V110C-A121C for binding with rabbit albumin, HER2 and streptavidin (SA), and probing with Fab-HRP or SA-HRP.
Figure 11:
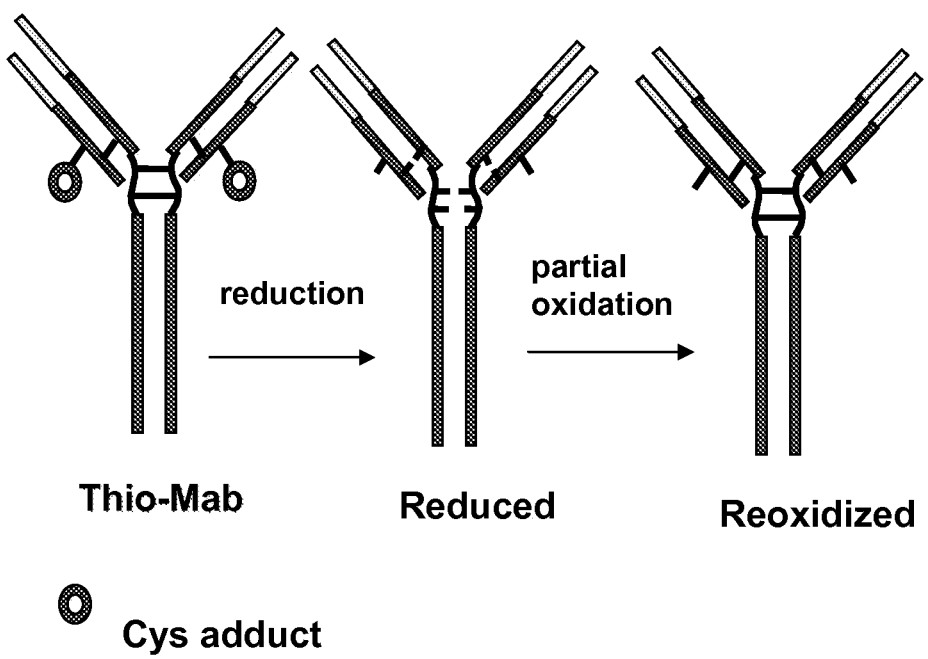
FIG. 11 shows the general process to prepare a cysteine engineered antibody (ThioMab) expressed from cell culture for conjugation.

(17) HER2 (ErbB2, Genbank accession no. M11730); Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4); Accession: P04626; EMBL; M11767; AAA35808.1. EMBL; M11761; AAA35808.1

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2); Accession: P40199; Q14920; EMBL; M29541; AAA59915.1. EMBL; M18728

Figure 8:
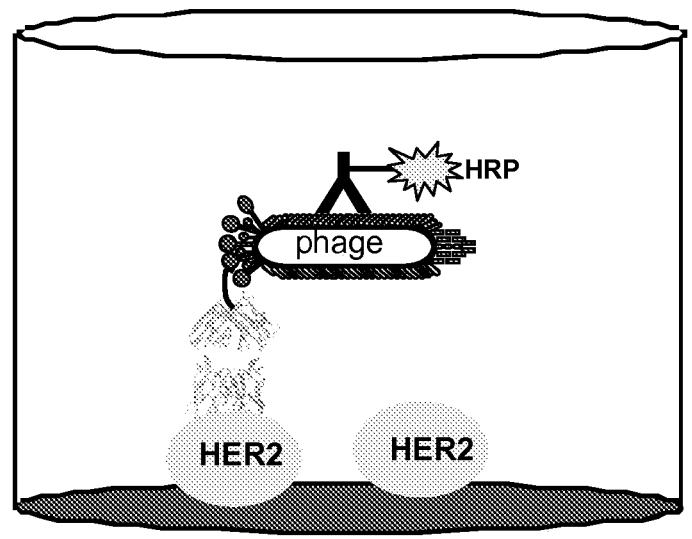
FIG. 8 shows binding of biotinylated ThioFab phage and an anti-phage HRP antibody to HER2 (top) and Streptavidin (bottom).
Figure 8:
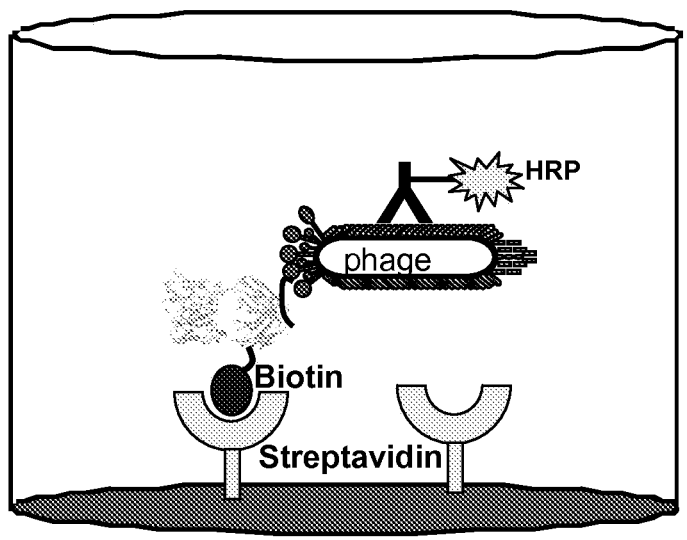

(19) MDP (DPEP1, Genbank accession no. BC017023); Proc. Natl. Acad. Sci. U.S.A. 99 (26):16899-16903 (2002)); WO2003016475 (claim 1); WO200264798 (claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59); Accession: Q9UHF4; Q6UWA9; Q96SH8; EMBL; AF184971; AAF01320.1.

(21) Brevican (BCAN, BEHAB, Genbank accession no. AF229053); Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1)

(22) EphB2R (DRT, ERK, Hek5, EPHT3, Tyro5, Genbank accession no. NM_004442); Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1

(23) ASLG659 (B7h, Genbank accession no. AX092328); US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318

(24) PSCA (Prostate stem cell antigen precursor, Genbank accession no. AJ297436); Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B); Accession: O43653; EMBL; AF043498; AAC39607.1

(25) GEDA (Genbank accession No. AY260763); AAP14954 lipoma HMGIC fusion-partner-like protein/pid=AAP14954.1—*Homo sapiens* (human); WO2003054152 (claim 20); WO2003000842 (claim 1); WO2003023013 (Example 3, claim 20); US2003194704 (claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens*: Thompson, J. S., et al Science 293 (5537), 2108-2111 (2001);

WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173:137-146; WO2003072036 (claim 1; FIG. 1); Cross-references: MIM: 107266; NP_001762.1; NM_001771_1

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11): 3457-3464

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1); WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779

(30) HLA-DOB (Beta subunit of MHC class II molecule (Ia antigen) that binds peptides and presents them to CD4+T lymphocytes); 273 aa, pI: 6.56, MW: 30820.TM: 1 [P] Gene Chromosome: 6p21.3, Genbank accession No. NP_002111.1); Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2); Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82)

(32) CD72 (B-cell differentiation antigen CD72, Lyb-2); 359 aa, pI: 8.66, MW: 40225, TM: 1 [P] Gene Chromosome: 9p13.3, Genbank accession No. NP_001773.1); WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1); US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1); WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21, Genbank accession No. Human:AF343662, AF343663, AF343664, AF343665, AF369794, AF397453, AK090423, AK090475, AL834187, AY358085; Mouse:AK089756, AY158090, AY506558; NP_112571.1; WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2): 178-84.

The parent antibody may also be a fusion protein comprising an albumin-binding peptide (ABP) sequence (Dennis et al. (2002) "Albumin Binding As A General Strategy For Improving The Pharmacokinetics Of Proteins" J Biol Chem. 277:35035-35043; WO 01/45746). Antibodies of the invention include fusion proteins with ABP sequences taught by:

(i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference.

Mutagenesis

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Site-directed mutagenesis is one method for preparing substitution variants, i.e. mutant proteins. This technique is well known in the art (see for example, Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed of protocols and formats, including those commercially available, e.g. QuikChange® Multi Site-Directed Mutagenesis Kit (Stratagene, La Jolla, CA).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. Oligonucleotides are prepared by the phosphoramidite synthesis method (U.S. Pat. Nos. 4,415,732; 4,458,066; Beaucage, S. and Iyer, R. (1992) "Advances in the synthesis of oligonucleotides by the phosphoramidite approach", Tetrahedron 48:2223-2311). This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

In the present invention, hu4D5Fabv8 displayed on M13 phage (Gerstner et al (2002) "Sequence Plasticity In The Antigen-Binding Site Of A Therapeutic Anti-HER2 Antibody", J Mol Biol. 321:851-62) was used for experiments as a model system. Cysteine mutations were introduced in hu4D5Fabv8-phage, hu4D5Fabv8, and ABP-hu4D5Fabv8 constructs. The hu4D5-ThioFab-Phage preps were carried out using the polyethylene glycol (PEG) precipitation method as described earlier (Lowman, Henry B. (1998) Methods in Molecular Biology (Totowa, New Jersey) 87 (Combinatorial Peptide Library Protocols) 249-264).

PHESELECTOR Assay

The PHESELECTOR (Phage ELISA for Selection of Reactive Thiols) assay allows for detection of reactive cysteine groups in antibodies in an ELISA phage format. The process of coating the protein (e.g. antibody) of interest on well surfaces, followed incubation with phage particles and then HRP labeled secondary antibody with absorbance detection is detailed in Example 2. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive. FIG. 8 illustrates the PHESELECTOR Assay by a schematic representation depicting the binding of Fab or ThioFab to HER2 (top) and biotinylated ThioFab to streptavidin (bottom).

Protein Expression and Purification

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or other mammalian host cells, such as myeloma cells (U.S. Pat. No. 5,807,715;

US 2005/0048572; US 2004/0229310) that do not otherwise produce the antibody protein, to obtain the synthesis of monoclonal antibodies in the recombinant host cells. The yields of hu4D5Fabv8 cysteine engineered antibodies were similar to wild type hu4D5Fabv8. Review articles on recombinant expression in bacteria of DNA encoding the antibody include Skerra et al (1993) Curr. Opinion in Immunol. 5:256-262 and Plückthun (1992) Immunol. Revs. 130:151-188.

After design and selection, cysteine engineered antibodies, e.g. ThioFabs, with highly reactive unpaired Cys residues, may be produced by: (i) expression in a bacterial, e.g. *E. coli*, system or a mammalian cell culture system (WO 01/00245), e.g. Chinese Hamster Ovary cells (CHO); and (ii) purification using common protein purification techniques (Lowman et al (1991) J. Biol. Chem. 266(17):10982-10988).

ThioFabs were expressed upon induction in 34B8, a non-suppressor *E. coli* strain (Baca et al (1997) Journal Biological Chemistry 272(16):10678-84). See Example 3a. The harvested cell pellet was resuspended in PBS (phosphate buffered saline), total cell lysis was performed by passing through a microfluidizer and the ThioFabs were purified by affinity chromatography with protein G SEPHAROSE™ (Amersham). ThioFabs were conjugated with biotin-PEO-maleimide as described above and the biotinylated-ThioFabs were further purified by Superdex-200™ (Amersham) gel filtration chromatography, which eliminated the free biotin-PEO-maleimide and the oligomeric fraction of ThioFabs.

Mass Spectroscopy Analysis

Liquid chromatography electrospray ionization mass spectrometric (LC-ESI-MS) analysis was employed for the accurate molecular weight determination of biotin conjugated Fab (Cole, R. B. Electro Spray Ionization Mass Spectrometry: Fundamentals, Instrumentation And Applications. (1997) Wiley, New York). The amino acid sequence of biotinylated hu4D5Fabv8 (A121C) peptide was determined by tryptic digestion followed by LC-ESI-Tandem MS analysis (Table 4, Example 3b).

The antibody Fab fragment hu4D5Fabv8 contains about 445 amino acid residues, including 10 Cys residues (five on the light and five on the heavy chain). The high-resolution structure of the humanized 4D5 variable fragment (Fv4D5) has been established, see: Eigenbrot et al "X-Ray Structures Of The Antigen-Binding Domains From Three Variants Of Humanized Anti-P185her2 Antibody 4D5 And Comparison With Molecular Modeling" (1993) J Mol Biol. 229:969-995). All the Cys residues are present in the form of disulfide bonds, therefore these residues do not have any reactive thiol groups to conjugate with drug-maleimide (unless treated with a reducing agent). Hence, the newly engineered Cys residue, can remain unpaired, and able to react with, i.e. conjugate to, an electrophilic linker reagent or drug-linker intermediate, such as a drug-maleimide. FIG. 1A shows a three-dimensional representation of the hu4D5Fabv8 antibody fragment derived by X-ray crystal coordinates. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, MD) for the 4d5v7fabH variant of trastuzumab according to FIG. 1B which shows the sequential numbering scheme (top row), starting at the N-terminus, differs from the Kabat numbering scheme (bottom row) by insertions noted by a,b,c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes in the following chart:

| 4D5Fab Heavy chain variants | Sequential Numbering | Kabat Numbering |
| --- | --- | --- |
| A40C | Ala-40 | Ala-40 |
| A88C | Ala-88 | Ala-84 |
| S119C | Ser-119 | Ser-112 |
| S120C | Ser-120 | Ser-113 |
| A121C | Ala-121 | Ala-114 |
| S122C | Ser-122 | Ser-115 |
| A175C | Ala-175 | Ala-168 |

M13 phagemid-Cys mutant Fabs (FIGS. 3A and 3B) can be rapidly screened compared to Fab proteins. Phagemid-ThioFab binding to antigen and to streptavidin can be tested by coating HER2 and streptavidin, respectively, onto ELISA plates followed by probing with anti-Fab-HRP (Horse radish peroxidase) as described in Example 2 and depicted in FIG. 8. This method allowed simultaneous monitoring of the effect on the antigen binding and the reactivity of the thiol group by the engineered Cys residue/conjugated biotin molecule. Also, the method can be applied to screen the reactive thiol groups for any protein displayed on M13 phage. Conjugated or unconjugated phagemid-ThioFabs are purified by simple PEG precipitation.

The antigen-binding fragment of humanized 4D5 (hu4D5Fab) is well expressed in *E. Coli* and has been displayed on bacteriophage (Garrard et al (1993) Gene 128:103-109). The antibody Fab fragment hu4D5Fabv8 was displayed on M13 phage as a model system in the ELISA based assay to probe thiol reactivity. FIG. 8 is a graphical representation of the PHESELECTOR assay, depicting binding of a biotinylated ThioFab phage and an anti-phage HRP antibody to HER2 (top) and Streptavidin (bottom). Five amino acid residues (L-Ala43, H-Ala40, H-Ser119, H-Ala121 and H-Ser122) were initially selected from crystal structure information as remote from the antigen binding surface (Eigenbrot et al. (1993) J Mol Biol. 229:969-995). The Protein Database X-ray crystal structure was designated as 1FVC. Cys residues were engineered at these positions by site directed mutagenesis. ThioFab-phage preparations were isolated and reacted with the biotinylation reagent.

Figure 2B:
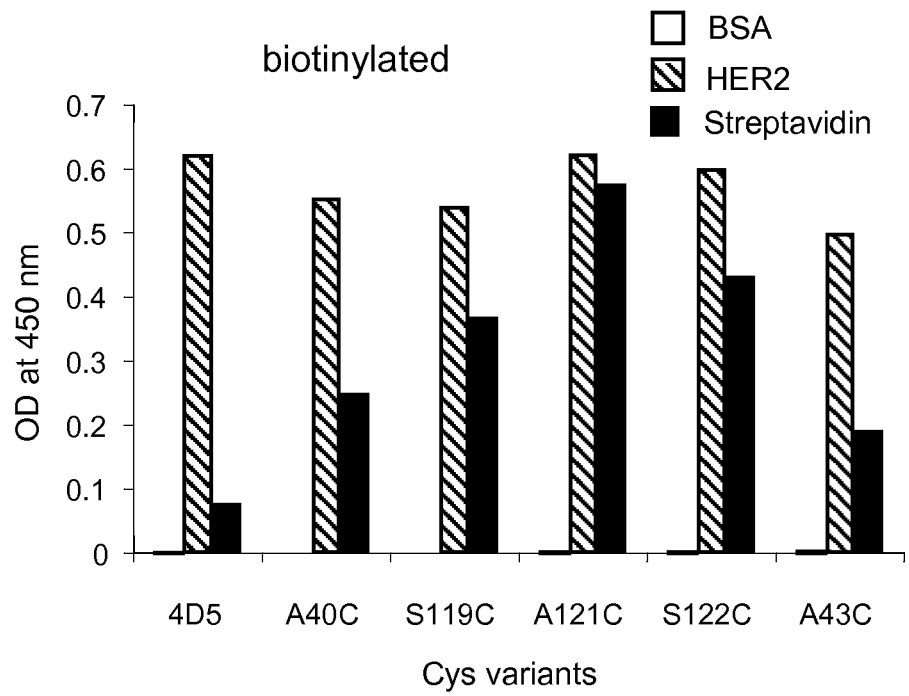

Biotin conjugated and unconjugated variants were tested for HER2 and streptavidin binding using an ELISA based PHESELECTOR assay (FIG. 8, Example 2) with an HRP (horseradish peroxidase)-conjugated anti-phage antibody. The interaction of non-biotinylated phage-hu4D5Fabv8 (FIG. 2A) and biotinylated phage-hu4D5Fabv8 (FIG. 2B) with BSA (open box), HER2 (grey box) or streptavidin (solid box) were monitored through anti-M13-horseradish peroxidase (HRP) antibody by developing a standard HRP reaction and measuring absorbance at 450 nm. The absorbance produced by turnover of a colorimetric substrate was measured at 450 nm. The reactivity of ThioFab with HER2 measures antigen binding. The reactivity of ThioFab with streptavidin measures the extent of biotinylation. The reactivity of ThioFab with BSA is a negative control for non-specific interaction. As seen in FIG. 2A, all the ThioFab-phage variants have similar binding to HER2 compared to that of wild type hu4D5Fabv8-phage. Furthermore, conjugation with biotin did not interfere in the ThioFab binding to HER2 (FIG. 2B).

Surprisingly and unexpectedly, the ThioFabs-phage samples showed varying levels of streptavidin binding activity. From all the tested phage-ThioFabs, the A121C cysteine engineered antibody exhibited maximal thiol reactivity. Even though wild type hu4D5Fabv8-phage was incubated with the same amounts of biotin-maleimide, these phage had little streptavidin binding indicating that preexisting cysteine residues (involved in disulfide bond formation) from the hu4D5Fabv8 and M13 phage coat proteins did not interfere with the site-specific conjugation of biotin-maleimide. These results demonstrate that the phage ELISA assay can be used successfully to screen reactive thiol groups on the Fab surface.

The PHESELECTOR assay allows screening of reactive thiol groups in antibodies. Identification of the A121C variant by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area (Å$^2$) that can be contacted by a solvent molecule, e.g. water. The occupied space of water is approximated as a 1.4 Å radius sphere. Software is freely available or licensable (Secretary to CCP4, Daresbury Laboratory, Warrington, WA4 4AD, United Kingdom, Fax: (+44) 1925 603825, or by internet: www.ccp4.ac.uk/dist/html/INDEX.html) as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J. Mol. Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file. AREAIMOL assumes a single radius for each element, and only recognizes a limited number of different elements. Unknown atom types (i.e. those not in AREAIMOL's internal database) will be assigned the default radius of 1.8 Å. The list of recognized atoms is:

| Atom | Atomic no. | Van der Waals rad. (Å) |
|---|---|---|
| C | 6 | 1.80 |
| N | 7 | 1.65 |
| O | 8 | 1.60 |
| Mg | 12 | 1.60 |
| S | 16 | 1.85 |
| P | 15 | 1.90 |

-continued

| Atom | Atomic no. | Van der Waals rad. (Å) |
|---|---|---|
| Cl | 17 | 1.80 |
| Co | 27 | 1.80 |

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100.

Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide.

The fractional surface accessibility for every amino acid in hu4D5Fabv7 was calculated using the crystal structure information (Eigenbrot et al. (1993) J Mol Biol. 229:969-995; U.S. Pat. No. 7,521,541). The following two criteria were applied to identify the residues of hu4D5Fabv8 that can be engineered to replace with Cys residues:

1. Amino acid residues that are completely buried are eliminated, i.e. less than 10% fractional surface accessibility. There are 134 (light chain) and 151 (heavy chain) residues of hu4D5Fabv8 that are more than 10% accessible (fractional surface accessibility). The top ten most accessible Ser, Ala and Val residues were selected due to their close structural similarity to Cys over other amino acids, introducing only minimal structural constraints in the antibody by newly engineered Cys. Other cysteine replacement sites can also be screened, and may be useful for conjugation.

2. Residues are sorted based on their role in functional and structural interactions of Fab. The residues which are not involved in antigen interactions and distant from the existing disulfide bonds were further selected. The newly engineered Cys residues should be distinct from, and not interfere with, antigen binding nor mispair with cysteines involved in disulfide bond formation.

Thiol reactivity may be generalized to any antibody where substitution of amino acids with reactive cysteine amino acids may be made within the ranges in the light chain selected from: L-10 to L-20; L-38 to L-48; L-105 to L-115; L-139 to L-149; L-163 to L-173; and within the ranges in the heavy chain selected from: H-35 to H-45; H-83 to H-93; H-114 to H-127; and H-170 to H-184, and in the Fc region within the ranges selected from H-268 to H-291; H-319 to H-344; H-370 to H-380; and H-395 to H-405.

Thiol reactivity may also be generalized to certain domains of an antibody, such as the light chain constant domain (CL) and heavy chain constant domains, CH1, CH2 and CH3. Cysteine replacements resulting in thiol reactivity values of about 0.8 and higher may be made in the heavy chain constant domains α, δ, ε, γ, and μ of intact antibodies: IgA, IgD, IgE, IgG, and IgM, respectively, including the IgG subclasses: IgG1, IgG2, IgG3, IgG4, IgA, and IgA2.

Figure 3A:
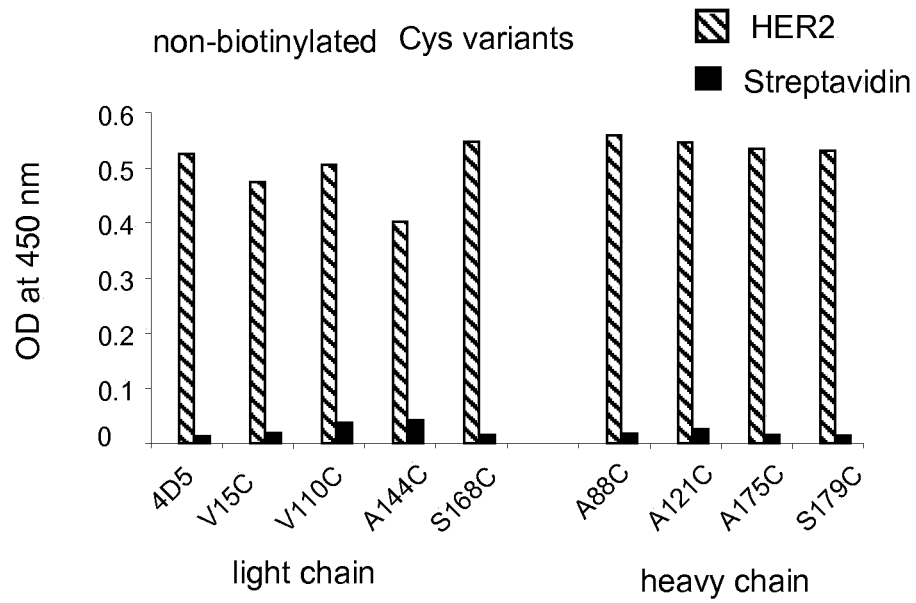
FIGS. 3A and 3B show binding measurements with detection of absorbance at 450 nm of hu4D5Fabv8 (left) and hu4D5Fabv8 Cys mutant (ThioFab) variants: (A) non-biotinylated phage-hu4D5Fabv8 and (B) biotinylated phage-hu4D5Fabv8 by the PHESELECTOR assay for interactions with: BSA (open bar), HER2 (striped bar) and streptavidin (solid bar). Light chain variants are on the left side and heavy chain variants are on the right side. Thiol reactivity=$OD_{450}$ nm for streptavidin binding÷ $OD_{450}$ for HER2 (antibody) binding
Figure 3B:
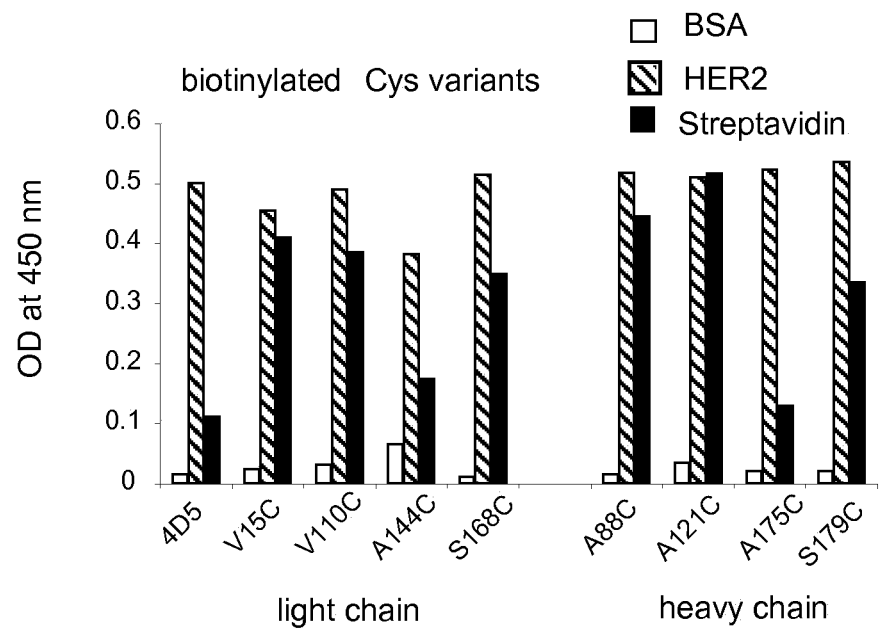

It is evident from the crystal structure data that the selected 10 Cys mutants are far away from the antigencombining site, such as the interface with HER2 in this case. These mutants can be tested experimentally for indirect effects on functional interactions. The thiol reactivities of all the Cys Fab variants were measured and calculated as described in Examples 1 and 2, and presented in Table 1. The residues L-V15C, L-V110C, H-A88C and H-A121C have reactive and stable thiol groups (FIGS. 3A and 3B). Mutants V15C, V110C, A144C, S168C are light chain Cys variants. Mutants A88C, A121C, A175C, S179C are heavy chain Cys variants. It was surprising and unexpected that the sites with high fractional surface accessibility did not have the highest thiol reactivity as calculated by the PHESELECTOR assay (Table 1). In other words, fractional surface accessibility (FIG. 1A) did not correlate with thiol reactivity (Table 1). In fact, the Cys residues engineered at the sites with moderate surface accessibility of 20% to 80% (FIG. 4A), or partially exposed sites, like Ala or Val residues, exhibited better thiol reactivity, i.e. >0.6, (FIG. 3B, Table 1) than the Cys introduced at Ser residues, thus necessitating the use of PHE-SELECTOR assay in the screening of thiol reactive sites since the crystal structure information alone is not sufficient to select these sites (FIGS. 3B and 4A).

Thiol reactivity data is shown in FIGS. 3A and 3B for amino acid residues of 4D5 ThioFab Cys mutants: (3A) non-biotinylated (control) and (3B) biotinylated phage-ThioFabs. Reactive thiol groups on antibody/Fab surface were identified by PHESELECTOR assay analyses for the interaction of non-biotinylated phage-hu4D5Fabv8 (3A) and biotinylated phage-hu4D5Fabv8 (3B) with BSA (open box), HER2 (grey box) or streptavidin (solid box). The assay was carried out as described in Example 2. Light chain variants are on the left side and heavy chain variants are on the right side. The binding of non-biotinylated 4D5 ThioFab Cys mutants is low as expected, but strong binding to HER2 is retained. The ratio of binding to streptavidin and to HER2 of the biotinylated 4D5 ThioFab Cys mutants gives the thiol reactivity values in Table 1. Background absorbance at 450 nm or small amounts of non-specific protein binding of the biotinylated 4D5 ThioFab Cys mutants to BSA is also evident in FIG. 3B. Fractional Surface Accessibility values of the selected amino acid residues that were replaced with a Cys residue are shown in FIG. 4A. Fractional surface accessibility was calculated from the available hu4D5Fabv7 structure (Eigenbrot et al. (1993) J Mol Biol. 229:969-995). The conformational parameters of the hu4D5Fabv7 and hu4D5Fabv8 structures are highly consistent and allow for determination of any correlation between fractional surface accessibility calculations of hu4D5Fabv7 and thiol reactivity of hu4D5Fabv8 cysteine mutants. The measured thiol reactivity of phage ThioFab Cys residues introduced at partially exposed residues (Ala or Val) have better thiol reactivity compared to the ones introduced at Ser residues (Table 1). It can be seen from the ThioFab Cys mutants of Table 1 that there is little or no correlation between thio reactivity values and fractional surface accessibility.

Amino acids at positions L-15, L-43, L-110, L-144, L-168, H-40, H-88, H-119, H-121, H-122, H-175, and H-179 of an antibody may generally be mutated (replaced) with free cysteine amino acids. Ranges within about 5 amino acid residues on each side of these positions may also be replaced with free cysteine acids, i.e. L-10 to L-20; L-38 to L-48; L-105 to L-115; L-139 to L-149; L-163 to L-173; H-35 to H-45; H-83 to H-93; H-114 to H-127; and H-170 to H-184, as well as the ranges in the Fc region selected from H-268 to H-291; H-319 to H-344; H-370 to H-380; and H-395 to H-405, to yield the cysteine engineered antibodies of the invention.

TABLE 1

Thiol reactivity of phage-ThioFabs

| Phage-ThioFab construct | Thiol Reactivity* | Fractional Surface Accessibility (%) (from Table 1) |
|---|---|---|
| hu4D5Fabv8-wt | 0.125 | — |
| L-V15C | 0.934 | 52.46 |
| L-A43C | 0.385 | 26.80 |
| L-V110C | 0.850 | 44.84 |
| L-A144C | 0.373 | 23.65 |
| L-S168C | 0.514 | 79.68 |
| H-A40C | 0.450 | 21.97 |
| H-A88C | 0.914 | 51.60 |
| H-S119C | 0.680 | 18.88 |
| H-A121C | 0.925 | 33.05 |
| H-S122C | 0.720 | 72.87 |
| H-A175C | 0.19 | 23.80 |
| H-S179C | 0.446 | 99.48 |

L = light chain,
H = heavy chain,
A = alanine,
S = serine,
V = valine,
C = cysteine
*Thiol reactivity is measured as the ratio of $OD_{450\,nm}$ for streptavidin binding to $OD_{450\,nm}$ for HER2 (antibody) binding (Example 2). Thiol reactivity value of 1 indicates complete biotinylation of the cysteine thiol.

Two Cys variants from light chain (L-V15C and L-V110C) and two from heavy chain (H-A88C and H-A121C) were selected for further analysis as these variants showed the highest thiol reactivity (Table 1).

Unlike phage purification, Fab preparation may require 2-3 days, depending on the scale of production. During this time, thiol groups may lose reactivity due to oxidation. To probe the stability of thiol groups on hu4D5Fabv8-phage, stability of the thiol reactivity of phage-thioFabs was measured (FIG. 4B). After ThioFab-phage purification, on day 1, day 2 and day 4, all the samples were conjugated with biotin-PEO-maleimide and probed with phage ELISA assay (PHESELECTOR) to test HER2 and streptavidin binding. L-V15C, L-V110C, H-A88C and H-A121C retain significant amounts of thiol reactivity compared to other ThioFab variants (FIG. 4B).

Labelled Cysteine Engineered Antibodies

The cysteine engineered antibodies of the invention may be conjugated with any label moiety which can be covalently attached to the antibody through a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, NY; Lundblad R. L. (1991) Chemical Reagents for Protein Modification, 2nd ed. CRC Press, Boca Raton, FL). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

(a) Radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{89}$Zr, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in *Current Protocols in Immunology*, (1991) Volumes 1 and 2, Coligen et al, Ed. Wiley-Interscience, New York, NY, Pubs. Chelating ligands which may complex a metal ion include DOTA, DOTP, DOTMA, DTPA and TETA (Macrocyclics, Dallas, TX). Radionuclides can be targeted via complexation with the antibody-drug conjugates of the invention (Wu et al (2005) Nature Biotechnology 23(9): 1137-1146). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, TX). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210).

Metal-chelate complexes suitable as antibody labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in *Current Protocols in Immunology*, supra, for example. Fluorescent dyes and fluorescent label reagents include those which are commercially available from Invitrogen/Molecular Probes (Eugene, OR) and Pierce Biotechnology, Inc. (Rockford, IL).

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in *Methods in Enzym.* (ed J. Langone & H. Van Vunakis), Academic Press, New York, 73:147-166.

Examples of enzyme-substrate combinations (U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

A label may be indirectly conjugated with a cysteine engineered antibody. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in *Bioconjugate Techniques* Academic Press, San Diego).

The polypeptide variant of the present invention may be employed in any known assay method, such as ELISA, competitive binding assays, direct and indirect sandwich assays, and immunoprecipitation assays (Zola, (1987) *Monoclonal Antibodies: A Manual of Techniques*, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Labelled cysteine engineered antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al (2010) Nuclear Medicine and Biology, 37(3):289-297; Chen et al (2004) Bioconjugate Chem. 15:41-49; US 2010/0111856 (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, *Molecular Probes Handbook of Fluorescent Probes and Research Chemicals*, Molecular Probes, Inc.; Brinkley, 1992, Bioconjugate Chem. 3:2; Garman, (1997) *Non-Radioactive Labelling: A Practical Approach*, Academic Press, London; Means (1990) Bioconjugate Chem. 1:2; Glazer et al (1975) *Chemical Modification of Proteins. Laboratory Techniques in Biochemistry and Molecular Biology* (T. S. Work and E. Work, Eds.) American Elsevier Publishing Co., New York; Lundblad, R. L. and Noyes, C. M. (1984) *Chemical Reagents for Protein Modification*, Vols. I and II, CRC Press, New York; Pfleiderer, G. (1985) "Chemical Modification of Proteins", *Modern Methods in Protein Chemistry*, H. Tschesche, Ed., Walter DeGryter, Berlin and New York; and Wong (1991) *Chemistry of Protein Conjugation and Cross-linking*, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer at pH 5.0 that will release the antigen from the polypeptide variant.

Labelling reagents typically bear reactive functionality which may react (i) directly with a cysteine thiol of a cysteine engineered antibody to form the labelled antibody, (ii) with a linker reagent to form a linker-label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

Conjugation of Biotin-Maleimide to Thiofabs

The above-described ThioFab properties were established in the presence of phage because fusion of the Fab to the phage coat protein could potentially alter Cys thiol accessibility or reactivity. Therefore, the ThioFab constructs were cloned into an expression vector under alkaline phosphatase promoter (Chang et al (1987) Gene 55:189-196) and the ThioFab expression was induced by growing *E. coli* cells in the phosphate-free medium. ThioFabs were purified on a Protein G SEPHAROSE™ column and analyzed on reducing and non-reducing SDS-PAGE gels. These analyses allow assessment of whether ThioFabs retained their reactive thiol group or were rendered inactive by forming intramolecular or intermolecular disulfide bonds. ThioFabs L-V15C, L-V110C, H-A88C, and H-A121C were expressed and purified by Protein-G SEPHAROSE™ column chromatography (see methods sections for details). Purified proteins were analyzed on SDS-PAGE gel in reducing (with DTT) and non-reducing (without DTT) conditions. Other reducing agents such as BME (beta-mercaptoethanol) can used in the gel to cleave interchain disulfide groups. It is evident from SDS-PAGE gel analysis that the major (~90%) fraction of ThioFab is in the monomeric form, while wild type hu4D5Fabv8 is essentially in the monomeric form (47 kDa).

ThioFab (A121C) and wild type hu4D5Fabv8 were incubated with 100 fold excess of biotin-maleimide for 3 hours at room temperature and the biotinylated Fabs were loaded onto a Superdex-200™ gel filtration column. This purification step was useful in separating monomeric Fab from oligomeric Fab and also from excess free biotin-maleimide (or free cytotoxic drug).

Figure 5:
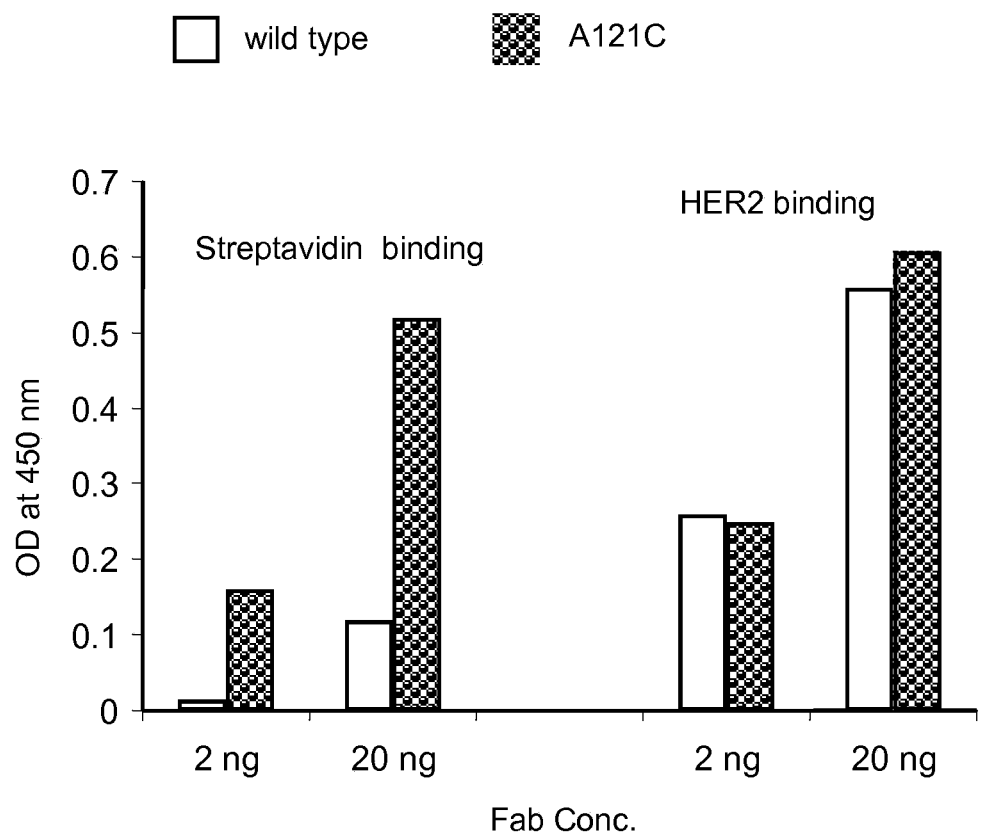
FIG. 5 shows binding measurements with detection of absorbance at 450 nm of biotin-maleimide conjugated-hu4D5Fabv8 (A121C) and non-biotinylated wild type hu4D5Fabv8 for binding to streptavidin and HER2. Each Fab was tested at 2 ng and 20 ng.

FIG. 5 shows validation of the properties of ThioFab variants in the absence of the phage context. The proteins without phage fusion, hu4D5Fabv8 and hu4D5Fabv8-A121C (ThioFab-A121C), were expressed and purified using protein-G agarose beads followed by incubation with 100 fold molar excess of biotin-maleimide. Streptavidin and HER2 binding of a biotinylated cys engineered ThioFab and a non-biotinylated wild type Fab was compared. The extent of biotin conjugation (interaction with streptavidin) and their binding ability to HER2 were monitored by ELISA analyses. Each Fab was tested at 2 ng and 20 ng.

Biotinylated A121C ThioFab retained comparable HER2 binding to that of wild type hu4D5Fabv8 (FIG. 5). Wild type Fab and A121C-ThioFab were purified by gel filtration column chromatography. The two samples were tested for HER2 and streptavidin binding by ELISA using goat anti-Fab-HRP as secondary antibody. Both wild type (open box) and ThioFab (dotted box) have similar binding to HER2 but only ThioFab retained streptavidin binding. Only a background level of interaction with streptavidin was observed with non-biotinylated wild type hu4D5Fabv8 (FIG. 5). Mass spectral (LC-ESI-MS) analysis of biotinylated-ThioFab (A121C) resulted in a major peak with 48294.5 daltons compared to the wild type hu4D5Fabv8 (47737 daltons). The 537.5 daltons difference between the two molecules exactly corresponds to a single biotin-maleimide conjugated to the ThioFab. Mass spec protein sequencing (LC-ESI-Tandem mass spec analysis) results further confirmed that the conjugated biotin molecule was at the newly engineered Cys residue (Table 8, Example 3b).

Site Specific Conjugation of Biotin-Maleimide to Albumin Binding Peptide (ABP)-Thiofabs Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827). A series of albumin binding peptides were identified by phage display screening (Dennis et al. (2002) "Albumin Binding As A General Strategy For Improving The Pharmacokinetics Of Proteins" J Biol Chem. 277:35035-35043; WO 01/45746). Compounds of the invention include ABP sequences taught by: (i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference.

Albumin Binding (ABP)-Fabs were engineered by fusing an albumin binding peptide to the C-terminus of Fab heavy chain in 1:1 stoichiometric ratio (1 ABP/1 Fab). It was shown that association of these ABP-Fabs with albumin increased their half life by more than 25 fold in rabbits and mice. The above described reactive Cys residues can therefore be introduced in these ABP-Fabs and used for site-specific conjugation with cytotoxic drugs followed by in vivo animal studies.

Exemplary albumin binding peptide sequences include, but are not limited to the amino acid sequences listed in SEQ ID NOS: 1-5:

```
                                          SEQ ID NO: 1
CDKTHTGGGSQRLMEDICLPRWGCLWEDDF

SEQ ID NO: 2
QRLMEDICLPRWGCLWEDDF

SEQ ID NO: 3
QRLIEDICLPRWGCLWEDDF

SEQ ID NO: 4
RLIEDICLPRWGCLWEDD

SEQ ID NO: 5
DICLPRWGCLW
```

The albumin binding peptide (ABP) sequences bind albumin from multiple species (mouse, rat, rabbit, bovine, rhesus, baboon, and human) with Kd (rabbit)=0.3 μM. The albumin binding peptide does not compete with ligands known to bind albumin and has a half life (T½) in rabbit of 2.3 hr. ABP-ThioFab proteins were purified on BSA-SEPHAROSE™ followed by biotin-maleimide conjugation and purification on Superdex-S200 column chromatography as described in previous sections. Purified biotinylated proteins were homogeneous and devoid of any oligomeric forms (Example 4).

FIG. 6 shows the properties of Albumin Binding Peptide (ABP)-ThioFab variants. ELISA analyses were carried out to test the binding ability of ABP-hu4D5Fabv8-wt, ABP-hu4D5Fabv8-V110C and ABP-hu4D5Fabv8-A121C with rabbit albumin, streptavidin and HER2. Biotinylated ABP-ThioFabs are capable of binding to albumin and HER2 with similar affinity to that of wild type ABP-hu4D5Fabv8 as confirmed by ELISA (FIG. 6) and BIAcore binding kinetics analysis (Table 2). An ELISA plate was coated with albumin, HER2 and SA as described. Binding of biotinylated ABP-ThioFabs to albumin, HER2 and SA was probed with anti-Fab HRP. Biotinylated ABP-ThioFabs were capable of binding to streptavidin compared to non biotinylated control ABP-hu4D5Fabv8-wt indicating that ABP-ThioFabs were conjugated with biotin maleimide like ThioFabs in a site specific manner as the same Cys mutants were used for both the variants (FIG. 6).

TABLE 2

BIAcore kinetic analysis for HER2 and rabbit albumin binding to biotinylated ABP- hu4D5Fabv8 wild type and ThioFabs

| Antibody | $k_{on}$ (M$^{-1}$s$^{-1}$) | $k_{off}$ (s$^{-1}$) | $K_d$ (nM) |
|---|---|---|---|
| HER2 binding | | | |
| wild type | 4.57 × 10$^5$ | 4.19 × 10$^{-5}$ | 0.0917 |
| V110C | 4.18 × 10$^5$ | 4.05 × 10$^{-5}$ | 0.097 |
| A121C | 3.91 × 10$^5$ | 4.15 × 10$^{-5}$ | 0.106 |
| Rabbit albumin binding | | | |
| wild type | 1.66 × 10$^5$ | 0.0206 | 124 |
| V110C | 2.43 × 10$^5$ | 0.0331 | 136 |
| A121C | 1.70 × 10$^5$ | 0.0238 | 140 |

ABP = albumin binding peptide

Alternatively, an albumin-binding peptide may be linked to the antibody by covalent attachment through a linker moiety.

Engineering of ABP-Thiofabs with Two Free Thiol Groups Per Fab

The above results indicate that all four (L-V15C, L-V110C, H-A88C and H-A121C) thioFab (cysteine engineered Fab antibodies) variants have reactive thiol groups that can be used for site specific conjugation with a label reagent, linker reagent, or drug-linker intermediate. L-V15C can be expressed and purified but with relatively low yields. However the expression and purification yields of L-V110C, H-A88C and H-A121C variants were similar to that of hu4D5Fabv8. Therefore these mutants can be used for further analysis and recombined to get more than one thiol group per Fab. Towards this objective, one thiol group on the light and one on heavy chain were constructed to obtain two thiol groups per Fab molecule (L-V110C/H-A88C and L-V110C/H-A121C). These two double Cys variants were expressed in an *E. coli* expression system and purified. The homogeneity of purified biotinylated ABP-ThioFabs was found to be similar to that of single Cys variants.

The effects of engineering two reactive Cys residues per Fab was investigated (FIG. 7). The presence of a second biotin was tested by probing the binding of biotinylated ABP-ThioFab to SA using streptavidin-HRP (FIG. 7). For HER2/Fab analysis, an ELISA plate was coated with HER2 and probed with anti-Fab HRP. For SA/Fab analysis, an ELISA plate was coated with SA and probed with anti-Fab HRP. For SA/SA analysis, an ELISA plate was coated with SA and probed with SA-HRP. FIG. 7. ELISA analyses for the interaction of biotinylated ABP-hu4D5Fabv8 cys variants with HER2, streptavidin (SA). HER2/Fab, SA/Fab and SA/SA indicate that their interactions were monitored by anti-Fab-HRP, SA-HRP, respectively. SA/Fab monitors the presence of single biotin per Fab and more than one biotin per Fab is monitored by SA/SA analysis. Binding of HER2 with double cys mutants is similar to that of single Cys variants (FIG. 7). However the extent of biotinylation on double Cys mutants was higher compared to single Cys variants due to more than one free thiol group per Fab molecule (FIG. 7).

Engineering of Thio IgG Variants of Trastuzumab

Cysteine was introduced into the full-length monoclonal antibody, trastuzumab (HERCEPTIN®, Genentech Inc.) at certain residues. The single cys mutants H-A88C, H-A121C and L-V110C of trastuzumab, and double cys mutants V110C-A121C and V110C-A121C of trastuzumab were expressed in CHO (Chinese Hamster Ovary) cells by transient fermentation in media containing 1 mM cysteine. The A88C mutant heavy chain sequence (450 aa) is SEQ ID NO:6. The A121C mutant heavy chain sequence (450 aa) is SEQ ID NO:7. The V110C mutant light chain sequence (214 aa) is SEQ ID NO:8.

```
                                          SEQ ID NO: 6
EVQLVESGGGLVQPGGSLRLSCAASGFNIKDTYIHWVRQAPGKGLEWVARI

YPTNGYTRYADSVKGRFTISADTSKNTAYLQMNSLRCEDTAVYYCSRWGGD

GFYAMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 7
EVQLVESGGGLVQPGGSLRLSCAASGFNIKDTYIHWVRQAPGKGLEWVARI

YPTNGYTRYADSVKGRFTISADTSKNTAYLQMNSLRAEDTAVYYCSRWGGD

GFYAMDYWGQGTLVTVSSCSTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 8
DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIKRTCAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC
```

According to one embodiment, the cysteine engineered thio-trastuzumab antibodies comprise one or more of the following variable region heavy chain sequences with a free cysteine amino acid (SEQ ID NOS: 9-16).

| Mutant | Sequence      | SEQ ID NO:    |
|--------|---------------|---------------|
| A40C   | WVRQCPGKGL    | SEQ ID NO: 9  |
| A88C   | NSLRCEDTAV    | SEQ ID NO: 10 |
| S119C  | LVTVCSASTKGPS | SEQ ID NO: 11 |
| S120C  | LVTVSCASTKGPS | SEQ ID NO: 12 |
| A121C  | LVTVSSCSTKGPS | SEQ ID NO: 13 |
| S122C  | LVTVSSACTKGPS | SEQ ID NO: 14 |
| A175C  | HTFPCVLQSSGLYS | SEQ ID NO: 15 |
| S179C  | HTFPAVLQCSGLYS | SEQ ID NO: 16 |

According to another embodiment, the cysteine engineered thio-trastuzumab antibodies comprise one or more of the following variable region light chain sequences with a free cysteine amino acid (SEQ ID NOS: 17-27).

| Mutant | Sequence      | SEQ ID NO:    |
|--------|---------------|---------------|
| V15C   | SLSASCGDRVT   | SEQ ID NO: 17 |
| A43C   | QKPGKCPKLLI   | SEQ ID NO: 18 |
| V110C  | EIKRTCAAPSV   | SEQ ID NO: 19 |
| 5S114C | TCAAPCVFIFPP  | SEQ ID NO: 20 |
| S121C  | FIFPPCDEQLK   | SEQ ID NO: 21 |
| S127C  | DEQLKCGTASV   | SEQ ID NO: 22 |
| A144C  | FYPRECKVQWK   | SEQ ID NO: 23 |

| Mutant | Sequence | SEQ ID NO: |
|---|---|---|
| A153C | WKVDNCLQSGN | SEQ ID NO: 24 |
| N158C | ALQSGCSQESV | SEQ ID NO: 25 |
| S168C | VTEQDCKDSTY | SEQ ID NO: 26 |
| V205C | GLSSPCTKSFN | SEQ ID NO: 27 |

Figure 10A:
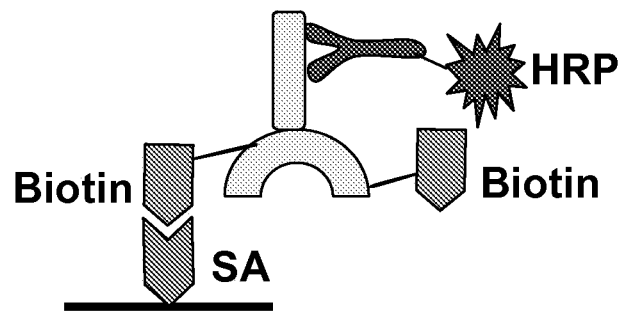
FIG. 10A shows a cartoon depiction of biotinylated antibody binding to immobilized HER2 with binding of biotin to anti-IgG-HRP for absorbance detection.
Figure 10B:
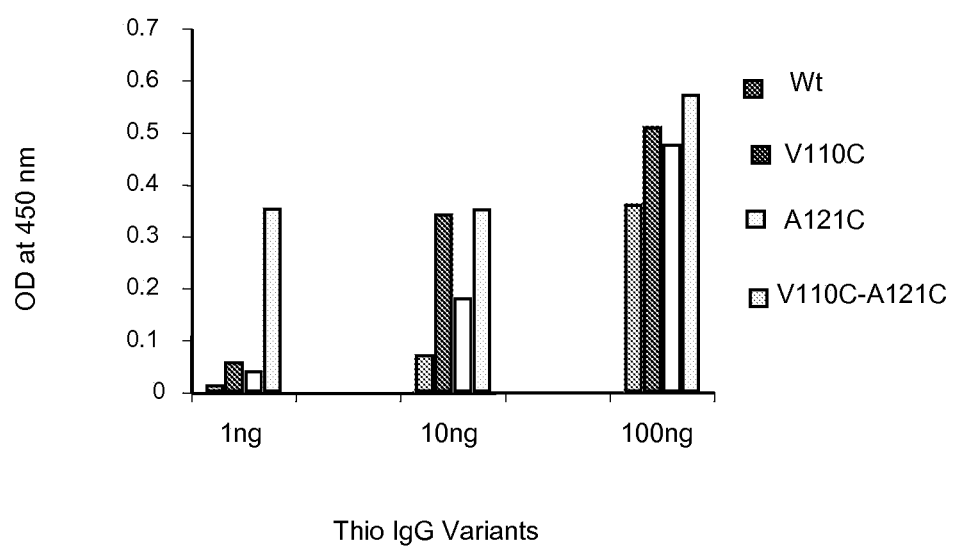
FIG. 10B shows binding measurements with detection of absorbance at 450 nm of biotin-maleimide conjugated-thio trastuzumab variants and non-biotinylated wild type trastuzumab in binding to immobilized streptavidin. From left to right: V110C (single cys), A121C (single cys), V110C/A121C (double cys), and trastuzumab. Each thio IgG variant and trastuzumab was tested at 1, 10, and 100 ng.

The resulting full-length, thio-trastuzumab IgG variants were assayed for thiol reactivity and HER2 binding activity. FIG. 10A shows a cartoon depiction of biotinylated antibody binding to immobilized HER2 and HRP labeled secondary antibody for absorbance detection. FIG. 10B shows binding measurements to immobilized HER2 with detection of absorbance at 450 nm of (left to right): non-biotinylated wild type trastuzumab (Wt), biotin-maleimide conjugated thio-trastuzumab variants V110C (single cys), A121C (single cys), and V110C-A121C (double cys). Each thio IgG variant and trastuzumab was tested at 1, 10, and 100 ng. The measurements show that biotinylated anti-HER2 ThioMabs retain HER2 binding activity.

FIG. 11A shows a cartoon depiction of a biotinylated antibody binding to immobilized HER2 with binding of biotin to anti-IgG-HRP for absorbance detection. FIG. 14B shows binding measurements with detection of absorbance at 450 nm of biotin-maleimide conjugated thio-trastuzumab variants and non-biotinylated wild type trastuzumab in binding to streptavidin. From left to right: V110C (single cys), A121C (single cys), V110C/A121C (double cys), and trastuzumab. Each thio IgG trastuzumab variant and parent trastuzumab was tested at 1, 10, and 100 ng. The measurements show that the HER2 ThioMabs have high thiol reactivity.

Cysteine was introduced into the full-length 2H9 anti-EphB2R antibody at certain residues. The single cys mutant H-A121C of 2H9 was expressed in CHO (Chinese Hamster Ovary) cells by transient fermentation in media containing 1 mM cysteine. The A121C 2H9 mutant heavy chain sequence (450 aa) is SEQ ID NO:28.

SEQ ID NO: 28
EVQLVESGGGLVQPGGSLRLSCAASGYTFTSYWMHWVRQAPGKGLEWVGFI
NPSTGYTDYNQKFKDRFTISADTSKNTAYLQMNSLRAEDTAVYYCTRRPKI
PRHANVFWGQGTLVTVSSCSTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

Cysteine engineered thio-2H9 antibodies comprise the following Fc constant region heavy chain sequences with a free cysteine amino acid (SEQ ID NOS: 29-38).

| Mutant | Sequence | SEQ ID NO: |
|---|---|---|
| V273C | HEDPECKFNWYVDGVEVHNAKTKPR | SEQ ID NO: 29 |
| V279C | HEDPEVKFNWYCDGVEVHNAKTKPR | SEQ ID NO: 30 |
| V282C | HEDPEVKFNWYVDGCEVHNAKTKPR | SEQ ID NO: 31 |
| V284C | HEDPEVKFNWYVDGVECHNAKTKPR | SEQ ID NO: 32 |
| A287C | HEDPEVKFNWYVDGVEVHNCKTKPR | SEQ ID NO: 33 |
| S324C | YKCKVCNKALP | SEQ ID NO: 34 |
| S337C | IEKTICKAKGQPR | SEQ ID NO: 35 |
| A339C | IEKTISKCKGQPR | SEQ ID NO: 36 |
| S375C | KGFYPCDIAVE | SEQ ID NO: 37 |
| S400C | PPVLDCDGSFF | SEQ ID NO: 38 |

Cysteine was introduced into the full-length 3A5 anti-MUC16 antibody at certain residues. The single cys mutant H-A121C of 3A5 was expressed in CHO (Chinese Hamster Ovary) cells by transient fermentation in media containing 1 mM cysteine. The A121C 3A5 mutant heavy chain sequence (446 aa) comprises SEQ ID NO:39.

SEQ ID NO: 39
DVQLQESGPGLVNPSQSLSLTCTVTGYSITNDYAWNWIRQFPGNKLEWMGY
INYSGYTTYNPSLKSRISITRDTSKNQFFLHLNSVTTEDTATYYCARWDGG
LTYWGQGTLVTVSACSTKGPSVFPLAPSSKSTSGGTAALGCLVKDYFPEPV
TVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSK
LTVDKSRWQQGNVFSCSVMHEALHNHYTQKSLSLSPGK

Cysteine engineered thio-3A5 anti-MUC16 antibodies comprise the following variable region heavy chain sequences with a free cysteine amino acid (SEQ ID NOS: 40-44).

| Mutant | Sequence | SEQ ID NO: |
|---|---|---|
| F45C | NWIRQCPGNK | SEQ ID NO: 40 |
| A90C | LNSCTTEDTAT | SEQ ID NO: 41 |
| A121C | GQGTLVTVSACSTKGPSVFPL | SEQ ID NO: 42 |
| A175C | HTFPCVLQSSGLYS | SEQ ID NO: 43 |
| V176C | HTFPACLQSSGLYS | SEQ ID NO: 44 |

Cysteine engineered thio-3A5 anti-MUC16 antibodies comprise the following variable region light chain sequences with a free cysteine amino acid (SEQ ID NOS: 45-49).

| Mutant | Sequence | SEQ ID NO: |
|---|---|---|
| L15C | FLSVSCGGRVT | SEQ ID NO: 45 |
| A43C | QKPGNCPRLLI | SEQ ID NO: 46 |

-continued

| Mutant | Sequence | SEQ ID NO: |
|---|---|---|
| V110C | EIKRTCAAPSV | SEQ ID NO: 47 |
| A144C | FYPRECKVQWK | SEQ ID NO: 48 |
| S168C | VTEQDCKDSTY | SEQ ID NO: 49 |

Engineering and Thiol Reactivity of 4D5 Anti-Her2 Thio-fabs

Cysteine was introduced into each position of the heavy chain and light chain of the anti-HER2 hu4D5Fabv8 Fab fragment antibody. All 440 of the heavy chain mutants and light chain mutants were prepared according to the methods described herein. Thiol reactivity was measured according to the PHESELECTOR assay. Heavy chain sequences are numbered by the Sequential numbering system. Light chain sequences follow the Kabat numbering system. In the light chain, both Kabat and Sequential numbering denotes same numbers.

Heavy chain hu4D5Fabv8 mutants were selected for efficient binding to HER2 receptor protein (FIGS. 2 and 3) and thiol reactivity with the biotinylation reagent, Biotin-PEO-maleimide (Examples 1 and 2). Certain heavy chain mutants had limited or compromised binding to HER2 ECD because this is an important residue for antigen binding (HER2), located in CDRs in the variable region of the antibody-Fab. Some of the residues located in the constant domain of the Fabs also resulted in poor HER2 binding because these residues may contribute to structure and folding of Fab, thus resulting in poor 4D5-Fab display on M13-page (Junutula, J. R. et al. (2008) J. Immunol Methods, 332:41-52). Heavy chain hu4D5Fabv8 mutants with poor HER2 ECD binding included cysteine mutations at positions 1, 21, 31, 33-36, 38, 48-50, 59, 87, 95, 101, 104, 129, 131, 132, 136, 153, 155, 159, 166, 169, 170, 172, 197, 198, 202, 215, 219. Wild type cysteine variants 22, 96, 147, 203, 223 were measured. Other heavy chain mutants had limited thiol reactivity with the biotinylation reagent. The free cysteine amino acid residue is in the center with flanking residues in the sequences in the middle column of Table 3. The substituted amino acid and position in the heavy chain are designated in the left column. Heavy chain hu4D5Fabv8 mutants SEQ ID NOS: 50-98 of Table 3 have retained HER2 binding and thiol reactivity values of about 0.8 or higher, excluding wild type cysteine variants. Antibodies with SEQ ID NOS: 50-98 (Table 3) have demonstrated thiol reactivity and may be useful to form covalent attachments with a capture label, a detection label, a drug moiety, or a solid support. The heavy chain mutants of Table 3 may be conjugated as ThioFabs or ThioMabs for example as antibody-drug conjugates.

TABLE 3

Efficient binding, thiol-reactive heavy chain hu4D5Fabv8 mutants

| HC-L4C | EVQCVESGG | SEQ ID NO: 50 |
|---|---|---|
| HC-G8C | QLVESCGGLVQ | SEQ ID NO: 51 |
| HC-G10C | VESGGCLVQPG | SEQ ID NO: 52 |
| HC-L20C | GGSLRCSCAAS | SEQ ID NO: 53 |
| HC-A23C | LRLSCCASGFN | SEQ ID NO: 54 |
| HC-G26C | SCAASCFNIKD | SEQ ID NO: 55 |
| HC-F27C | CAASGCNIKDT | SEQ ID NO: 56 |
| HC-T32C | FNIKDCYIHWV | SEQ ID NO: 57 |
| HC-Q39C | IHWVRCAPGKG | SEQ ID NO: 58 |
| HC-P41C | WVRQACGKGLE | SEQ ID NO: 59 |
| HC-K43C | RQAPGCGLEWV | SEQ ID NO: 60 |
| HC-G44C | QAPGKCLEWVA | SEQ ID NO: 61 |
| HC-W47C | GKGLECVARIY | SEQ ID NO: 62 |
| HC-S63C | TRYADCVKGRF | SEQ ID NO: 63 |
| HC-F68C | SVKGRCTISAD | SEQ ID NO: 64 |
| HC-D73C | FTISACTSKNT | SEQ ID NO: 65 |
| HC-K76C | SADTSCNTAYL | SEQ ID NO: 66 |
| HC-T78C | DTSKNCAYLQM | SEQ ID NO: 67 |
| HC-Y80C | SKNTACLQMNS | SEQ ID NO: 68 |
| HC-L81C | KNTAYCQMNSL | SEQ ID NO: 69 |
| HC-Q82C | NTAYLCMNSLR | SEQ ID NO: 70 |
| HC-L86C | LQMNSCRAEDT | SEQ ID NO: 71 |

TABLE 3-continued

Efficient binding, thiol-reactive heavy chain hu4D5Fabv8 mutants

| | | |
|---|---|---|
| HC-A88C | MNSLRCEDTAV | SEQ ID NO: 72 |
| HC-D90C | SLRAECTAVYY | SEQ ID NO: 73 |
| HC-V93C | AEDTACYYCSR | SEQ ID NO: 74 |
| HC-Y94C | EDTAVCYCSRW | SEQ ID NO: 75 |
| HC-R98C | VYYCSCWGGDG | SEQ ID NO: 76 |
| HC-G100C | YCSRWCGDGFY | SEQ ID NO: 77 |
| HC-D108C | GFYAMCYWGQG | SEQ ID NO: 78 |
| HC-G113C | DYWGQCTLVTV | SEQ ID NO: 79 |
| HC-T117C | QGTLVCVSSAS | SEQ ID NO: 80 |
| HC-A121C | VTVSSCSTKGP | SEQ ID NO: 81 |
| HC-G125C | SASTKCPSVFP | SEQ ID NO: 82 |
| HC-G141C | KSTSGCTAALG | SEQ ID NO: 83 |
| HC-P154C | VKDYFCEPVTV | SEQ ID NO: 84 |
| HC-N162C | VTVSWCSGALT | SEQ ID NO: 85 |
| HC-S163C | TVSWNCGALTS | SEQ ID NO: 86 |
| HC-G164C | VSWNSCALTSG | SEQ ID NO: 87 |
| HC-S168C | SGALTCGVHTF | SEQ ID NO: 88 |
| HC-F173C | SGVHTCPAVLQ | SEQ ID NO: 89 |
| HC-T190C | LSSVVCVPSSS | SEQ ID NO: 90 |
| HC-S194C | VTVPSCSLGTQ | SEQ ID NO: 91 |
| HC-T200C | SLGTQCYICNV | SEQ ID NO: 92 |
| HC-V205C | TYICNCNHKPS | SEQ ID NO: 93 |
| HC-N211C | NHKPSCTKVDK | SEQ ID NO: 94 |
| HC-T212C | HKPSNCKVDKK | SEQ ID NO: 95 |
| HC-V214C | PSNTKCDKKVE | SEQ ID NO: 96 |
| HC-K217C | TKVDKCVEPKS | SEQ ID NO: 97 |
| HC-T226C | KSCDKCH | SEQ ID NO: 98 |

Light chain hu4D5Fabv8 mutants were selected for efficient binding to HER2 receptor protein (FIGS. 2 and 3) and thiol reactivity with the biotinylation reagent, Biotin-PEO-maleimide (Examples 1 and 2). Certain light chain mutants had limited or compromised binding to HER2 because this is an important residue for antigen binding (HER2), located in CDRs in the variable region of the antibody-Fab. Some of the residues located in constant domain of Fab also resulted in poor HER2 binding because these residues may contribute to structure and folding of Fab, thus resulting in poor 4D5-Fab display on M13-page (Junutula, J. R. et al. (2008) J. Immunol Methods, 332:41-52). Light chain hu4D5Fabv8 mutants with poor binding to HER2 included cysteine mutants at positions 4, 29-32, 35, 36, 50, 82, 86, 89-91, 113, 115, 117, 120, 126, 128, 139, 141, 146, 148, 179, 186, 192, 202. Wild type cysteine variants 23, 134, 194, 214 were measured. Other light chain mutants had limited thiol reactivity with the biotinylation reagent. The free cysteine amino acid residue is in the center with flanking residues in the sequences in the middle column of Table 4. The substituted amino acid and position in the light chain are designated in the left column. Light chain hu4D5Fabv8 mutants SEQ ID NOS: 99-147 of Table 4 have retained HER2 binding and thiol reactivity values of about 0.8 or higher, excluding wild type cysteine variants. Antibodies with SEQ ID NOS: 99-147 (Table 4) have demonstrated thiol reactivity and may be useful to form covalent attachments with a capture label, a detection label, a drug moiety, or a solid support. The light chain mutants of Table 4 may be conjugated as ThioFabs or ThioMabs for example as antibody-drug conjugates.

TABLE 4

Efficient binding, thiol-reactive light chain hu4D5Fabv8 mutants

| | | |
|---|---|---|
| LC-S9C | MTQSPCSLSAS | SEQ ID NO: 99 |
| LC-L46C | GKAPKCLIYSA | SEQ ID NO: 100 |
| LC-Y49C | PKLLICSASFL | SEQ ID NO: 101 |
| LC-F53C | IYSASCLYSGV | SEQ ID NO: 102 |
| LC-T72C | SGTDFCLTISS | SEQ ID NO: 103 |
| LC-L73C | GTDFTCTISSL | SEQ ID NO: 104 |
| LC-T74C | TDFTLCISSLQ | SEQ ID NO: 105 |
| LC-I75C | DFTLTCSSLQP | SEQ ID NO: 106 |
| LC-S77C | TLTISCLQPED | SEQ ID NO: 107 |
| LC-Q79C | TISSLCPEDFA | SEQ ID NO: 108 |
| LC-P80C | ISSLQCEDFAT | SEQ ID NO: 109 |
| LC-Y92C | YCQQHCTTPPT | SEQ ID NO: 110 |
| LC-P95C | QHYTTCPTFGQ | SEQ ID NO: 111 |
| LC-G99C | TPPTFCQGTKV | SEQ ID NO: 112 |
| LC-G101C | PTFGQCTKVEI | SEQ ID NO: 113 |
| LC-K103C | FGQGTCVEIKR | SEQ ID NO: 114 |
| LC-E105C | QGTKVCIKRTV | SEQ ID NO: 115 |
| LC-V110C | EIKRTCAAPSV | SEQ ID NO: 116 |
| LC-A112C | KRTVACPSVFI | SEQ ID NO: 117 |
| LC-S114C | TVAAPCVFIFP | SEQ ID NO: 118 |
| LC-F116C | AAPSVCIFPPS | SEQ ID NO: 119 |
| LC-F118C | PSVFICPPSDE | SEQ ID NO: 120 |
| LC-S121C | FIFPPCDEQLK | SEQ ID NO: 121 |
| LC-L125C | PSDEQCKSGTA | SEQ ID NO: 122 |
| LC-S127C | DEQLKCGTASV | SEQ ID NO: 123 |
| LC-T129C | QLKSGCASVVC | SEQ ID NO: 124 |
| LC-A130C | LKSGTCSVVCL | SEQ ID NO: 125 |
| LC-S131C | KSGTACVVCLL | SEQ ID NO: 126 |
| LC-N137C | VVCLLCNFYPR | SEQ ID NO: 127 |
| LC-N138C | VCLLNCFYPRE | SEQ ID NO: 128 |
| LC-Y140C | LLNNFCPREAK | SEQ ID NO: 129 |
| LC-R142C | NNFYPCEAKVQ | SEQ ID NO: 130 |
| LC-A144C | FYPRECKVQWK | SEQ ID NO: 131 |
| LC-Q147C | REAKVCWKVDN | SEQ ID NO: 132 |
| LC-K149C | AKVQWCVDNAL | SEQ ID NO: 133 |
| LC-D151C | VQWKVCNALQS | SEQ ID NO: 134 |
| LC-Q155C | VDNALCSGNSQ | SEQ ID NO: 135 |
| LC-Q160C | QSGNSCESVTE | SEQ ID NO: 136 |
| LC-A184C | LTLSKCDYEKH | SEQ ID NO: 137 |

TABLE 4-continued

Efficient binding, thiol-reactive light chain hu4D5Fabv8 mutants

| | | |
|---|---|---|
| LC-D185C | TLSKACYEKHK | SEQ ID NO: 138 |
| LC-K188C | KADYECHKVYA | SEQ ID NO: 139 |
| LC-T197C | YACEVCHQGLS | SEQ ID NO: 140 |
| LC-G200C | EVTHQCLSSPV | SEQ ID NO: 141 |
| LC-L201C | VTHQGCSSPVT | SEQ ID NO: 142 |
| LC-S203C | HQGLSCPVTKS | SEQ ID NO: 143 |
| LC-P204C | QGLSSCVTKSF | SEQ ID NO: 144 |
| LC-V205C | GLSSPCTKSFN | SEQ ID NO: 145 |
| LC-T206C | LSSPVCKSFNR | SEQ ID NO: 146 |
| LC-K207C | SSPVTCSFNRG | SEQ ID NO: 147 |

Thiol Reactivity of Thiomabs

The thiol reactivity of full length, IgG cysteine engineered antibodies (ThioMabs) was measured by biotinylation and streptavidin binding (U.S. Pat. No. 7,521,541). A western blot assay was set up to screen the ThioMab that is specifically conjugated with biotin-maleimide. In this assay, the antibodies are analyzed on reducing SDS-PAGE and the presence of Biotin is specifically probed by incubating with streptavidin-HRP. As seen from FIG. 18, the streptavidin-HRP interaction is either observed in heavy chain or light chain depending on which engineered cys variant is being used and no interaction is seen with wild type, indicating that ThioMab variants specifically conjugated the biotin at engineered Cys residue. FIG. 18 shows denaturing gel analysis of reduced, biotinylated Thio-IgG variants after capture on immobilized anti-IgG-HRP (top gel) and streptavidin-HRP (bottom gel). Lane 1: 3A5 H-A121C. Lane 2: 3A5 L-V110C. Lane 3: 2H9 H-A121C. Lane 4: 2H9 L-V110C. Lane 5: anti-EphB2R 2H9 parent, wild type. Each mutant (lanes 1-4) was captured by anti-IgG with HRP detection (top) indicating that selectivity and affinity were retained. Capture by immobilized streptavidin with HRP detection (bottom) confirmed the location of biotin on heavy and light chains. The location of cysteine mutation on the cysteine engineered antibodies in lanes 1 and 3 is the heavy chain. The location of cysteine mutation on the cysteine engineered antibodies in lanes 2 and 4 is the light chain. The cysteine mutation site undergoes conjugation with the biotin-maleimide reagent.

Analysis of the ThioMab cysteine engineered antibodies of FIG. 18 and a 2H9 V15C variant by LC/MS gave quantitative indication of thiol reactivity (Table 5).

TABLE 5

LC/MS quantitation of biotinylation of ThioMabs - Thiol reactivity

| ThioMab variant | number of biotin per ThioMab |
|---|---|
| 2H9 wt | 0.0 |
| 2H9 L-V15C | 0.6 |
| 2H9 L-V110C | 0.5 |
| 2H9 H-A121C | 2.0 |
| 3A5 L-V110C | 1.0 |
| 3A5 H-A121C | 2.0 |

Cysteine engineering was conducted in the constant domain, i.e. Fc region, of IgG antibodies. A variety of amino acid sites were converted to cysteine sites and the expressed mutants, i.e. cysteine engineered antibodies, were assessed for their thiol reactivity. Biotinylated 2H9 ThioMab Fc variants were assessed for thiol reactivity by HRP quantitation by capture on immobilized streptavidin in an ELISA assay (FIG. 19). An ELISA assay was established to rapidly screen the Cys residues with reactive Thiol groups. As depicted in FIG. 19 schematic diagram, the streptavidin-biotin interaction is monitored by probing with anti-IgG-HRP followed by measuring absorbance at 450 nm. These results confirmed 2H9-ThioFc variants V282C, A287C, A339C, S375C and S400C had moderate to highest Thiol reactivity. The extent of biotin conjugation of 2H9 ThioMab Fc variants was quantitated by LS/MS analysis as reported in Table 6. The LS/MS analysis confirmed that the A282C, S375C and S400C variants had 100% biotin conjugation and V284C and A339C had 50% conjugation, indicating the presence of a reactive cysteine thiol group. The other ThioFc variants, and the parent, wild type 2H9, had either very little biotinylation or none.

TABLE 6

LC/MS quantitation of biotinylation of 2H9 Fc ThioMabs

| 2H9 ThioMab Fc variant | % biotinylation |
|---|---|
| V273C | 0 |
| V279C | 31 |
| V282C | 100 |
| V284C | 50 |
| A287C | 0 |
| S324C | 71 |
| S337C | 0 |
| A339C | 54 |
| S375C | 100 |
| S400C | 100 |
| (wild type 2H9) | 0 |

Thiol Reactivity of Thio-4D5 Fab Light Chain Variants

Screening of a variety of cysteine engineered light chain variant Fabs of the antiErbB2 antibody 4D5 gave a number of variants with a thiol reactivity value of 0.6 and higher (Table 7), as measured by the PHESELECTOR assay of FIG. 8. The thiol reactivity values of Table 7 are normalized to the heavy chain 4D5 ThioFab variant (HC-A121C) which is set at 100%, assuming complete biotinylation of HC-A121C variant, and represented as percent values.

TABLE 7

Thiol reactivity per cent values of 4D5 ThioFab light chain variants

| 4D5 ThioFab variant | Thiol reactivity value (%) |
|---|---|
| V15C | 100 |
| V110C | 95 |
| S114C | 78 |
| S121C | 75 |
| S127C | 75 |
| A153C | 82 |
| N158C | 77 |
| V205C | 78 |
| (HC-A121C) | 100 |
| (4D5 wild type) | 25 |

Antibody-Drug Conjugates

The cysteine engineered antibodies of the invention may be conjugated with any therapeutic agent, i.e. drug moiety, which can be covalently attached to the antibody through a reactive cysteine thiol group.

An exemplary embodiment of an antibody-drug conjugate (ADC) compound comprises a cysteine engineered antibody (Ab), and a drug moiety (D) wherein the antibody has one or more free cysteine amino acids, and the antibody is attached through the one or more free cysteine amino acids by a linker moiety (L) to D; the composition having Formula I:

where p is 1, 2, 3, or 4. The number of drug moieties which may be conjugated via a thiol reactive linker moiety to an antibody molecule is limited by the number of cysteine residues which are introduced by the methods described herein. Exemplary ADC of Formula I therefore comprise antibodies which have 1, 2, 3, or 4 engineered cysteine amino acids.

Another exemplary embodiment of an antibody-drug conjugate compound (ADC) comprises a cysteine engineered antibody (Ab), an albumin-binding peptide (ABP) and a drug moiety (D) wherein the antibody is attached to the drug moiety by a linker moiety (L) and the antibody is attached to the albumin-binding peptide by an amide bond or a second linker moiety; the composition having Formula Ia:

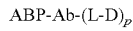

where p is 1, 2, 3, or 4.

The ADC compounds of the invention include those with utility for anticancer activity. In particular, the compounds include a cysteine-engineered antibody conjugated, i.e. covalently attached by a linker, to a drug moiety, i.e. toxin. When the drug is not conjugated to an antibody, the drug has a cytotoxic or cytostatic effect. The biological activity of the drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Drug Moieties

The drug moiety (D) of the antibody-drug conjugates (ADC) includes any compound, moiety or group which has a cytotoxic or cytostatic effect. Drug moieties include: (i) chemotherapeutic agents, which may function as microtubulin inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC1065, a calicheamicin and other enediyne antibiotics, a taxane, an anthracycline, and stereoisomers, isosteres, analogs or derivatives thereof.

Maytansine compounds suitable for use as maytansinoid drug moieties are well known in the art, and can be isolated from natural sources according to known methods, produced using genetic engineering techniques (see Yu et al (2002) PROC. NAT. ACAD. SCI. (USA) 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using Streptomyces or Actinomyces or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR)(U.S. Pat. No. 4,331,598); C-14-hydroxymethyl or acyloxymethyl (CH$_2$OH or CH2OAc) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

The drug moiety (D) of the antibody-drug conjugates (ADC) of Formula I include maytansinoids having the structure:

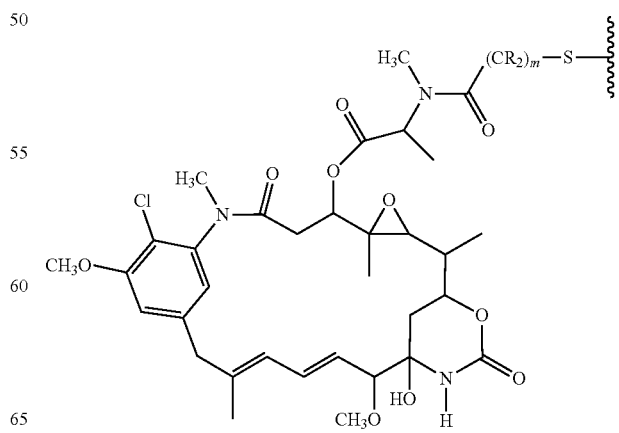

where the wavy line indicates the covalent attachment of the sulfur atom of D to a linker (L) of an antibody-drug conjugate (ADC). R may independently be H or a C1-C6 alkyl selected from methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. The alkylene chain attaching the amide group to the sulfur atom may be methanyl, ethanyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207).

Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines (US 2005/0169933; WO 2005/037992; U.S. Pat. No. 5,208,020).

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

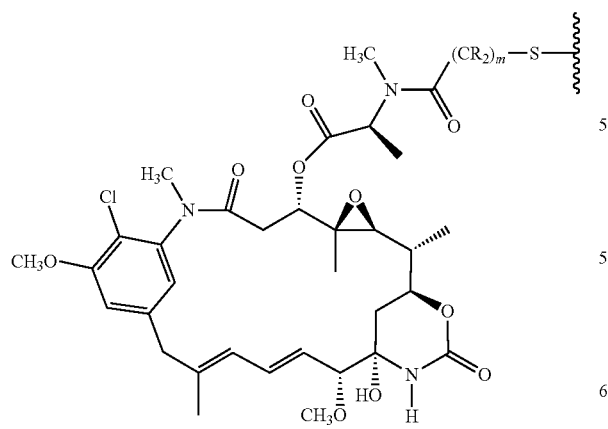

Exemplary embodiments of maytansinoid drug moieties include: DM1, $(CR_2)_m$=$CH_2CH_2$; DM3, $(CR_2)_m$=$CH_2CH_2CH(CH_3)$; and DM4, $(CR_2)_m$=$CH_2CH_2C(CH_3)_2$, having the structures:

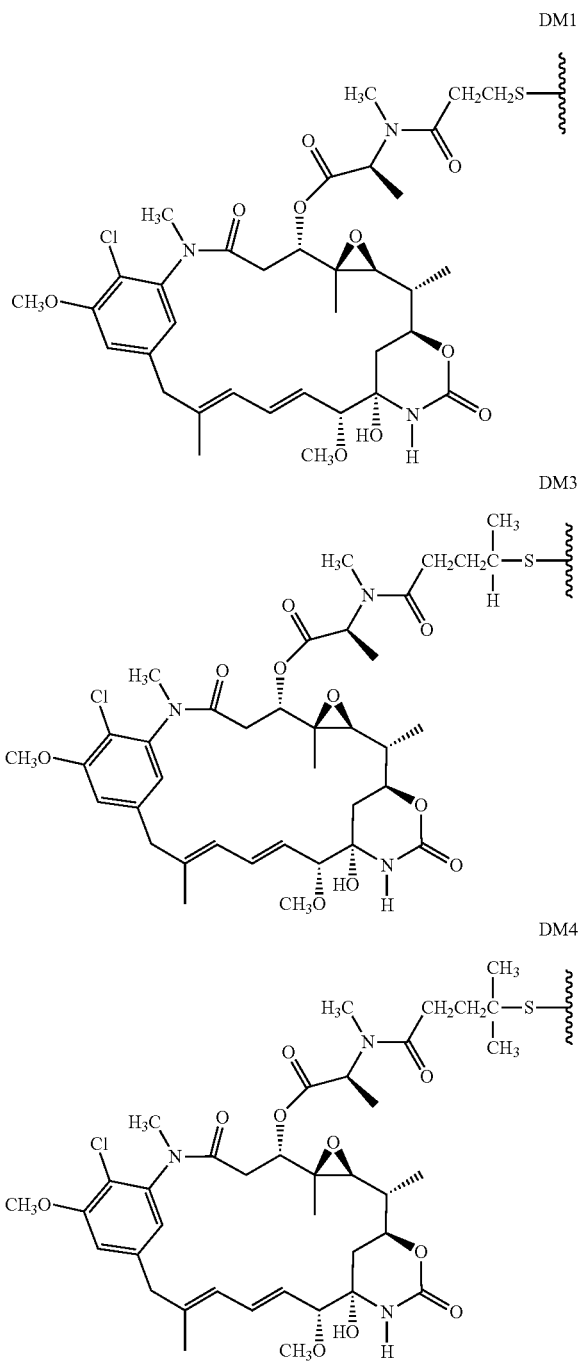

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

The drug moiety (D) of the antibody-drug conjugates (ADC) of Formula I also include dolastatins and their peptidic analogs and derivatives, the auristatins (U.S. Pat.

Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102(4):1458-1465).

Drug moieties include dolastatins, auristatins (U.S. Pat. Nos. 5,635,483; 5,780,588; 5,767,237; 6,124,431), and analogs and derivatives thereof. Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in U.S. Pat. Nos. 7,498,298 and 7,659,241, the disclosure of each which is expressly incorporated by reference in their entirety.

The drug moiety (D) of the antibody-drug conjugates (ADC) of Formula I include the monomethylauristatin drug moieties MMAE and MMAF linked through the N-terminus to the antibody, and having the structures:

limited to, $\gamma_1^I$, $\alpha_2^I$, $\alpha_3^I$, N-acetyl-$\gamma_1^I$, PSAG and $\theta_1^I$ (Hinman et al Cancer Research 53:3336-3342 (1993), Lode et al Cancer Research 58:2925-2928 (1998).

Protein toxins include: diphtheria A chain, nonbinding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include: $^{32}$P, $^{33}$P, $^{90}$Y, $^{125}$I, $^{131}$I, $^{131}$In, $^{153}$Sm, $^{186}$Re, $^{188}$Re, $^{211}$At, $^{212}$Bi, $^{212}$Pb, and radioactive isotopes of Lu.

The radioisotope or other labels may be incorporated in the conjugate in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triaminepentaacetic acid (MX-DTPA) is an exemplary chelating agent for conjugation of a radionuclide to the antibody (WO 94/11026).

Linkers

A "Linker" (L) is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a Linker having reactive functionality for binding to the Drug and to the Antibody. A cysteine thiol of a cysteine engineered antibody (Ab) can form a bond with a functional group of a linker reagent, a drug moiety or drug-linker intermediate.

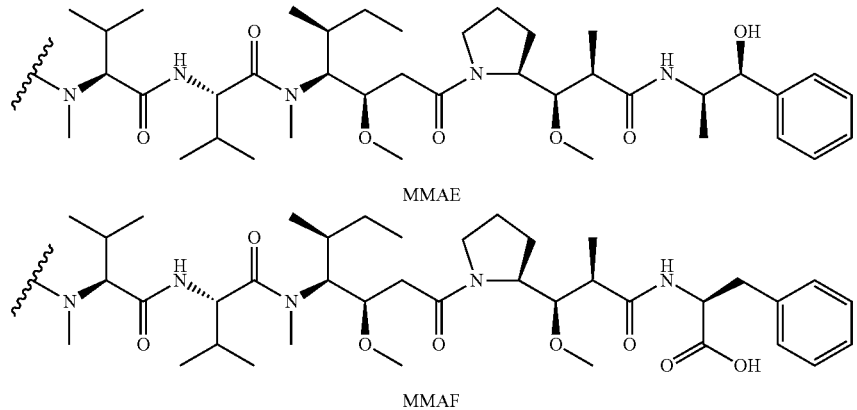

MMAE

MMAF

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

The drug moiety includes calicheamicin, and analogs and derivatives thereof. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; 5,877,296. Structural analogues of calicheamicin which may be used include, but are not In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Cysteine engineered antibodies react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773, and according to the protocol of Example 4.

In yet another embodiment, the reactive group of a linker reagent or drug-linker intermediate contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

The linker may comprise amino acid residues which links the antibody (Ab) to the drug moiety (D) of the cysteine engineered antibody-drug conjugate (ADC) of the invention. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as minor amino acids and non-naturally occurring amino acid analogs, such as citrulline.

Useful amino acid residue units can be designed and optimized in their selectivity for enzymatic cleavage by a particular enzymes, for example, a tumor-associated protease to liberate an active drug moiety. In one embodiment, an amino acid residue unit, such as valine-citrulline (vc or val-cit), is that whose cleavage is catalyzed by cathepsin B, C and D, or a plasmin protease.

A linker unit may be of the self-immolative type such as a p-aminobenzylcarbamoyl (PAB) unit where the ADC has the exemplary structure:

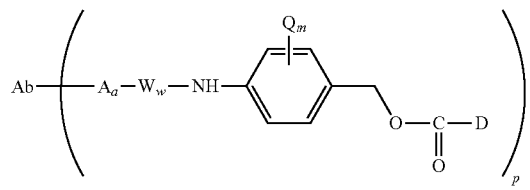

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (U.S. Pat. No. 7,375,078; Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker (WO 2004/01993; Szalai et al (2003) J. Amer. Chem. Soc. 125:15688-15689; Shamis et al (2004) J. Amer. Chem. Soc. 126:1726-1731; Amir et al (2003) Angew. Chem. Int. Ed. 42:4494-4499).

Embodiments of the Formula Ia antibody-drug conjugate compounds include (val-cit), (MC-val-cit), and (MC-val-cit-PAB):

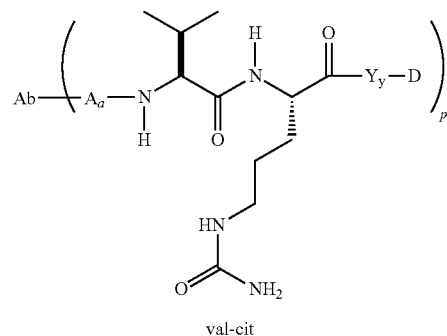

val-cit

-continued

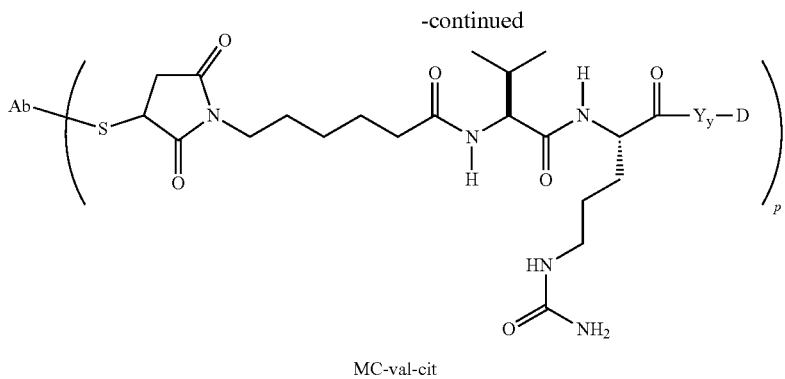
MC-val-cit

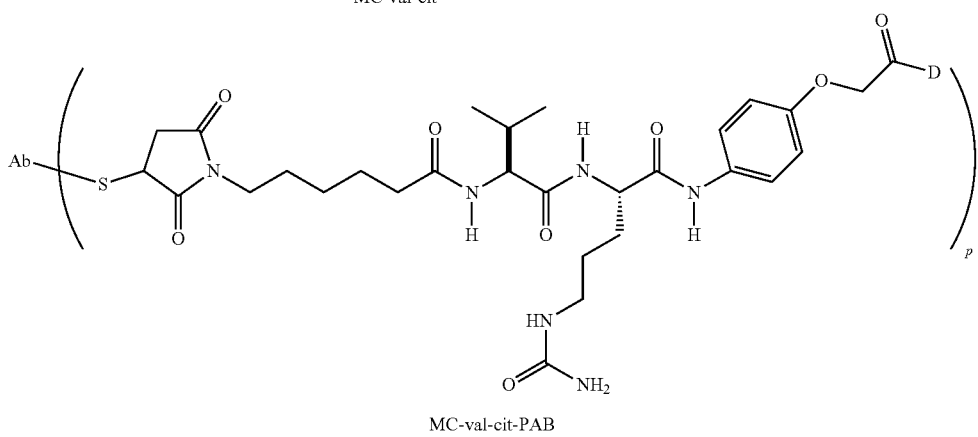
MC-val-cit-PAB

Other exemplary embodiments of the Formula Ia antibody-drug conjugate compounds include the structures:

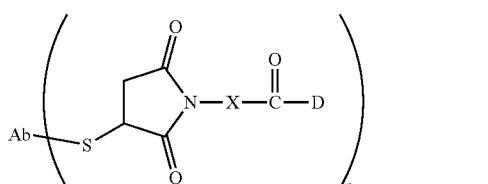

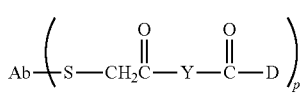

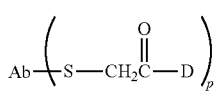

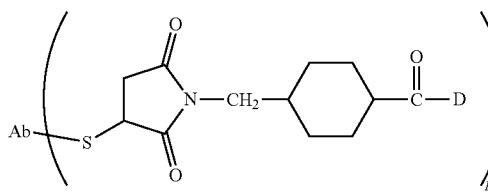

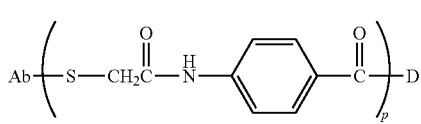

XIVd where X is:

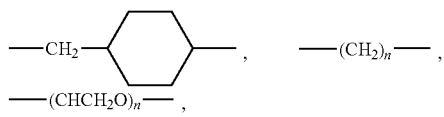

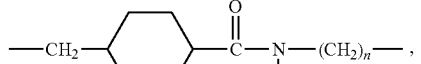

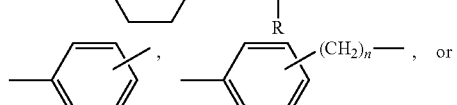

Y is:

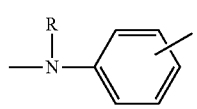

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schroder and K. Lake (1965) "The Peptides", volume 1, pp 76-136, Academic Press) which is well known in the field of peptide chemistry.

In another embodiment, the Linker may be substituted with groups which modulated solubility or reactivity. For example, a charged substituent such as sulfonate (—SO$_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

The compounds of the invention expressly contemplate, but are not limited to, ADC prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, IL 61105 U.S.A, 1-800-874-3723, International +815-968-0747. See pages 467-498, 2003-2004 Applications Handbook and Catalog. Bis-maleimide reagents allow the attachment of the thiol group of a cysteine engineered antibody to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

Useful linker reagents can also be obtained via other commercial sources, such as Molecular Biosciences Inc. (Boulder, CO), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

An exemplary valine-citrulline (val-cit or vc) dipeptide linker reagent having a maleimide Stretcher and a para-aminobenzylcarbamoyl (PAB) self-immolative Spacer has the structure:

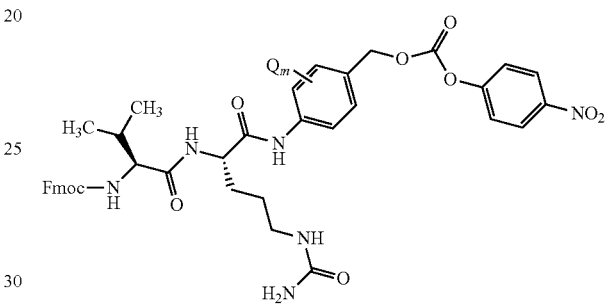

where Q is —C$_1$-C$_8$ alkyl, —O—(C$_1$-C$_8$ alkyl), -halogen, -nitro or -cyano; and m is an integer ranging from 0-4.

An exemplary phe-lys(Mtr) dipeptide linker reagent having a maleimide Stretcher unit and a p-aminobenzyl self-immolative Spacer unit can be prepared according to Dubowchik, et al. (1997) Tetrahedron Letters, 38:5257-60, and has the structure:

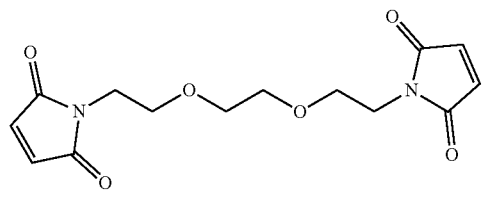

BM(PEO)$_2$

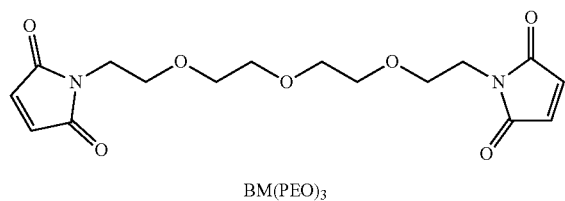

BM(PEO)$_3$

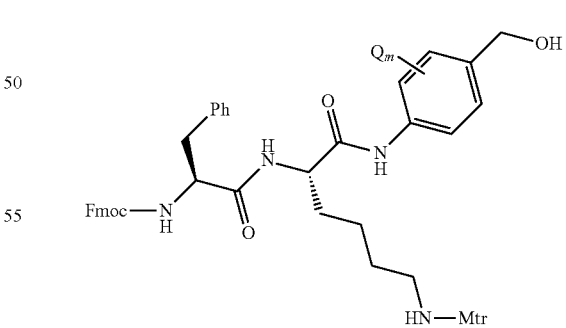

where Mtr is mono-4-methoxytrityl, Q is —C$_1$-C$_8$ alkyl, —O—(C$_1$-C$_8$ alkyl), -halogen, -nitro or -cyano; and m is an integer ranging from 0-4.

Exemplary antibody-drug conjugate compounds of the invention include:

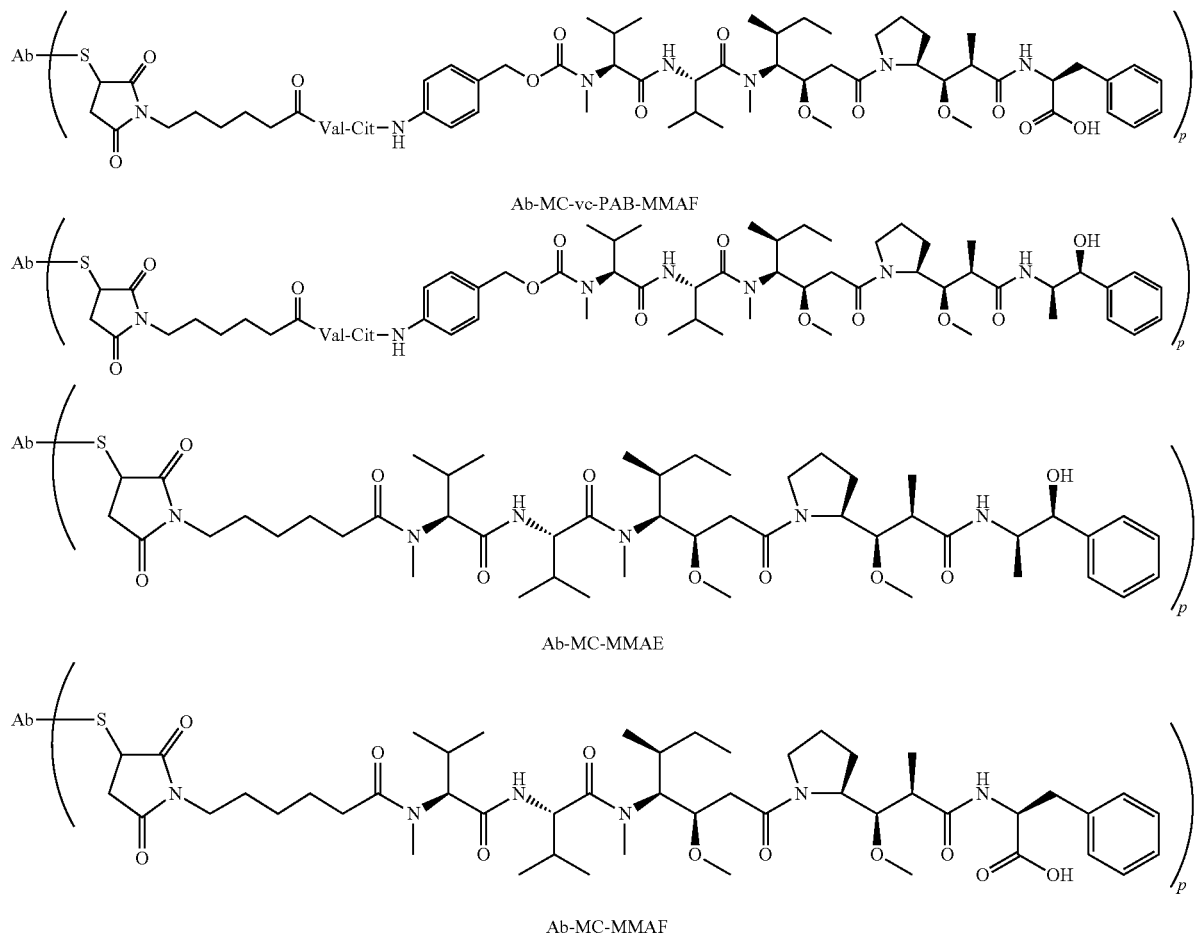
where Val is valine; Cit is citrulline; p is 1, 2, 3, or 4; and Ab is a cysteine engineered antibody. Other exemplary antibody drug conjugates where maytansinoid drug moiety DM1 is linked through a BMPEO linker to a thiol group of trastuzumab have the structure:
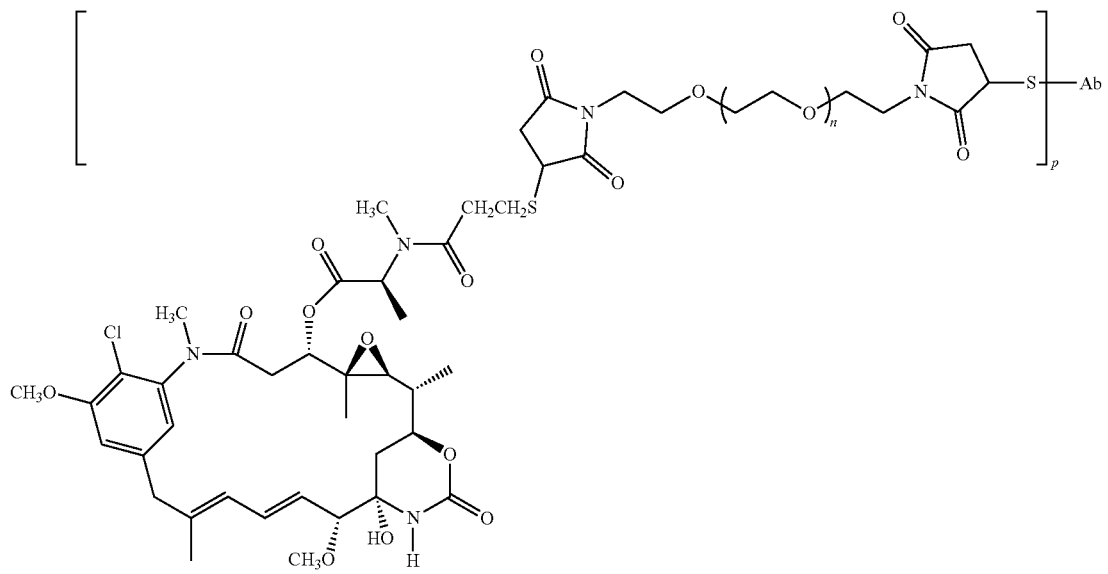

where Ab is a cysteine engineered antibody; n is 0, 1, or 2; and p is 1, 2, 3, or 4.

Preparation of Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Maytansine may, for example, be converted to May-SSCH3, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163, 5,208,020, 5,416,064; WO 01/024763). The disulfide linker SPP is constructed with linker reagent N-succinimidyl 4-(2-pyridylthio) pentanoate.

Under certain conditions, the cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, MA). Full length, cysteine engineered monoclonal antibodies (ThioMabs) expressed in CHO cells were reduced with about a 50 fold excess of TCEP for 3 hrs at 37° C. to reduce disulfide bonds which may form between the newly introduced cysteine residues and the cysteine present in the culture media. The reduced ThioMab was diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate ($CuSO_4$) at room temperature, overnight. Other oxidants, i.e. oxidizing agents, and oxidizing conditions, which are known in the art may be used. Ambient air oxidation is also effective. This mild, partial reoxidation step forms intrachain disulfides efficiently with high fidelity. An approximate 10 fold excess of drug-linker intermediate, e.g. $BM(PEO)_4$-DM1 was added, mixed, and let stand for about an hour at room temperature to effect conjugation and form the ThioMab antibody-drug conjugate. The conjugation mixture was gel filtered and loaded and eluted through a HiTrap S column to remove excess drug-linker intermediate and other impurities.

FIG. 11 shows the general process to prepare a cysteine engineered antibody expressed from cell culture for conjugation. Cysteine adducts, presumably along with various interchain disulfide bonds, are reductively cleaved to give a reduced form of the antibody. The interchain disulfide bonds between paired cysteine residues are reformed under partial oxidation conditions, such as exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs have to be treated with reduction and oxidation procedures as described in Example 11 to produce reactive ThioMabs. These ThioMabs are used to conjugate with maleimide containing cytotoxic drugs, fluorophores, and other labels.

A variety of ThioFab and ThioMab antibody-drug conjugates were prepared (Examples 4-8). Cysteine mutant hu4D5Fabv8 (V110C) was conjugated with the maytansinoid drug moiety DM1 with a bis-maleimido linker reagent BMPEO to form hu4D5Fabv8 (V110C)-BMPEO-DM1 (Example 8).

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody-drug conjugates was measured by a cell proliferation assay (FIGS. 10 and 11, Example 9). The CellTiter-Glo® Luminescent Cell Viability Assay is a commercially available (Promega Corp., Madison, WI), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

In Vivo Efficacy

The in vivo efficacy of two albumin binding peptide-DM1 (maytansinoid)-antibody-drug conjugates (ADC) of the invention is measured by a high expressing HER2 transgenic explant mouse model (FIG. 12, Example 10). An allograft is propagated from the Fo5 mmtv transgenic mouse which does not respond to, or responds poorly to, HERCEPTIN® therapy. Subjects were treated once with ABP-rhuFab4D5-cys(light chain)-DM1; ABP-rhuFab4D5-cys(heavy chain)-DM1; and placebo PBS buffer control (Vehicle) and monitored over 3 weeks to measure the time to tumor doubling, log cell kill, and tumor shrinkage.

Administration of Antibody-Drug Conjugates

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Antibody-Drug Conjugate Treatments

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-ErbB2 antibody. Other dosage regimens may be useful. The progress of this therapy is easily monitored by conventional techniques and assays.

Labelled Antibody Imaging Methods

In another embodiment of the invention, cysteine engineered antibodies may be labelled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labelled cysteine engineered antibody, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

commercially available biotinylation reagents with electrophilic groups which are reactive with cysteine thiol groups may be used, including Biotin-BMCC, PEO-Iodoacetyl Biotin, Iodoacetyl-LC-Biotin, and Biotin-HPDP (Pierce Biotechnology, Inc.), and $N^\alpha$-(3-maleimidylpropionyl)biocytin (MPB, Molecular Probes, Eugene, OR). Other commercial sources for biotinylation, bifunctional and multifunctional linker reagents include Molecular Probes, Eugene, OR, and Sigma, St. Louis, MO

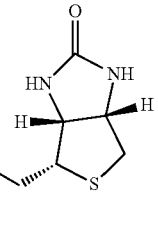

Biotin-PEO-maleimide

Example 2—PHESELECTOR Assay

Bovine serum albumin (BSA), erbB2 extracellular domain (HER2) and streptavidin (100 µl of 2 µg/ml) were separately coated on Maxisorp 96 well plates. After blocking with 0.5% Tween-20 (in PBS), biotinylated and non-biotinylated hu4D5Fabv8-ThioFab-Phage ($2\times10^{10}$ phage particles) were incubated for 1 hour at room temperature followed by incubation with horseradish peroxidase (HRP) labeled secondary antibody (anti-M13 phage coat protein, pVIII protein antibody). FIG. 8 illustrates the PHESELECTOR Assay by a schematic representation depicting the binding of Fab or ThioFab to HER2 (top) and biotinylated ThioFab to streptavidin (bottom).

Standard HRP reaction was carried out and the absorbance was measured at 450 nm. Thiol reactivity was measured by calculating the ratio between $OD_{450}$ for streptavidin/$OD_{450}$ for HER2. A thiol reactivity value of 1 indicates complete biotinylation of the cysteine thiol. In the case of Fab protein binding measurements, hu4D5Fabv8 (2-20 ng) was used followed by incubation with HRP labeled goat polyclonal anti-Fab antibodies.

EXAMPLES

Example 1—Preparation of Biotinylated ThioFab Phage

ThioFab-phage ($5\times10^{12}$ phage particles) were reacted with 150 fold excess of biotin-PEO-maleimide ((+)-biotinyl-3-maleimidopropionamidyl-3,6-dioxaoctainediamine, Oda et al (2001) Nature Biotechnology 19:379-382, Pierce Biotechnology, Inc.) for 3 hours at room temperature. Excess biotin-PEO-maleimide was removed from biotin-conjugated phage by repeated PEG precipitations (3-4 times). Other Example 3a—Expression and Purification of ThioFabs ThioFabs were expressed upon induction in 34B8, a non-suppressor E. coli strain (Baca et al (1997) Journal Biological Chemistry 272(16):10678-84). The harvested cell pellet was resuspended in PBS (phosphate buffered saline), total cell lysis was performed by passing through a microfluidizer and the ThioFabs were purified by affinity chromatography with protein G SEPHAROSE™ (Amersham).

ThioFabs L-V15C, L-V110C, H-A88C, and H-A121C were expressed and purified by Protein-G SEPHAROSE™ column chromatography. Oligomeric-Fab was present in fractions 26 to 30, and most of the monomeric form was in fractions 31-34. Fractions consisting of the monomeric form were pooled and analyzed by SDS-PAGE along with wild type hu4D5Fabv8 and analyzed on SDS-PAGE gel in reducing (with DTT or BME) and non-reducing (without DTT or BME) conditions. Gel filtration fractions of A121C-ThioFab were analyzed on non-reducing SDS-PAGE.

ThioFabs were conjugated with biotin-PEO-maleimide as described above and the biotinylated-ThioFabs were further purified by Superdex-200™ (Amersham) gel filtration chromatography, which eliminated the free biotin-PEO-maleimide and the oligomeric fraction of ThioFabs. Wild type hu4D5Fabv8 and hu4D5Fabv8 A121C-ThioFab (0.5 mg in quantity) were each and separately incubated with 100 fold molar excess of biotin-PEO-maleimide for 3 hours at room temperature and loaded onto a Superdex-200 gel filtration column to separate free biotin as well as oligomeric Fabs from the monomeric form.

Example 3b—Analysis of ThioFabs

Enzymatic digest fragments of biotinylated hu4D5Fabv8 (A121C) ThioFab and wild type hu4D5Fabv8 were analyzed by liquid chromatography electrospray ionization mass spectroscopy (LS-ESI-MS) The difference between the 48294.5 primary mass of biotinylated hu4D5Fabv8 (A121C) and the 47737.0 primary mass of wild type hu4D5Fabv8 was 557.5 mass units. This fragment indicates the presence of a single biotin-PEO-maleimide moiety ($C_{23}H_{36}N_5O_7S_2$). Table 8 shows assignment of the fragmentation values which confirms the sequence.

TABLE 8

LC-ESI-Mass spec analysis of biotinylated hu4D5Fabv8 ThioFab A121C after tryptic digestion

| Amino acid | b Fragment | y Fragment |
| --- | --- | --- |
| A (Alanine) | 72 | |
| M (Methionine) | 203 | 2505 |
| D (Aspartic acid) | 318 | 2374 |
| Y (Tyrosine) | 481 | 2259 |
| W (Tryptophan) | 667 | 2096 |
| G (Glycine) | 724 | 1910 |
| Q (glutamine) | 852 | 1853 |
| G (Glycine) | 909 | 1725 |
| T (Threonine) | 1010 | 1668 |
| L (Leucine) | 1123 | 1567 |
| V (Valine) | 1222 | 1454 |
| T (Threonine) | 1323 | 1355 |
| V (Valine) | 1422 | 1254 |
| S (Serine) | 1509 | 1155 |
| S (Serine) | 1596 | 1068 |
| C (Cysteine) + biotin | 2242 | 981 |
| S (Serine) | 2329 | 335 |
| T (Threonine) | 2430 | 248 |
| K (Lysine) | | 175 |

Before and after Superdex-200 gel filtration, SDS-PAGE gel analyses, with and without reduction by DTT or BME, of biotinylated ABP-hu4D5Fabv8-A121C, biotinylated ABP-hu4D5Fabv8-V110C, biotinylated double Cys ABP-hu4D5Fabv8-(V110C-A88C), and biotinylated double Cys ABP-hu4D5Fabv8-(V110C-A121C) were conducted.

Mass spectroscopy analysis (MS/MS) of hu4D5Fabv8-(V110C)-BMPEO-DM1 (after Superdex-200 gel filtration purification): Fab+1 51607.5, Fab 50515.5. This data shows 91.2% conjugation. MS/MS analysis of hu4D5Fabv8-(V110C)-BMPEO-DM1 (reduced): LC 23447.2, LC+1 24537.3, HC (Fab) 27072.5. This data shows that all DM1 conjugation is on the light chain of the Fab.

Example 4—Preparation of ABP-hu4D5Fabv8-(V110C)-MC-MMAE by Conjugation of ABP-hu4D5Fabv8-(V110C) and MC-MMAE The drug linker reagent, maleimidocaproyl-monomethyl auristatin E (MMAE), i.e. MC-MMAE, dissolved in DMSO, is diluted in acetonitrile and water at known concentration, and added to chilled ABP-hu4D5Fabv8-(V110C) ThioFab in phosphate buffered saline (PBS) according to U.S. Pat. Nos. 7,521,541, 7,659,241, and 7,498,298. After about one hour, an excess of maleimide is added to quench the reaction and cap any unreacted antibody thiol groups. The reaction mixture is concentrated by centrifugal ultrafiltration and ABP-hu4D5Fabv8-(V110C)-MC-MMAE is purified and desalted by elution through G25 resin in PBS, filtered through 0.2 μm filters under sterile conditions, and frozen for storage.

Example 5—Preparation of ABP-hu4D5Fabv8-(LC V110C)-MC-MMAF by Conjugation of ABP-hu4D5Fabv8-(LC V110C) and MC-MMAF ABP-hu4D5Fabv8-(LC V110C)-MC-MMAF is prepared by conjugation of ABP-hu4D5Fabv8-(LC V110C) ThioFab and MC-MMAF following the procedure of Example 4.

Example 6—Preparation of ABP-HC A121C-Thio-Fab-MC-Val-Cit-PAB-MMAE by Conjugation of ABP-HC A121C-ThioFab and MC-Val-Cit-PAB-MMAE ABP-hu4D5Fabv8-(HC A121C)-MC-val-cit-PAB-MMAE is prepared by conjugation of ABP-hu4D5Fabv8-(HC A121C) and MC-val-cit-PAB-MMAE following the procedure of Example 4.

Example 7—Preparation of ABP-HC A121C-Thio-Fab-MC-Val-Cit-PAB-MMAF by Conjugation of ABP-HC A121C-ThioFab and MC-Val-Cit-PAB-MMAF ABP-hu4D5Fabv8-(HC A121C)-MC-val-cit-PAB-MMAF is prepared by conjugation of ABP-hu4D5Fabv8-(HC A121C) and MC-val-cit-PAB-MMAF following the procedure of Example 4.

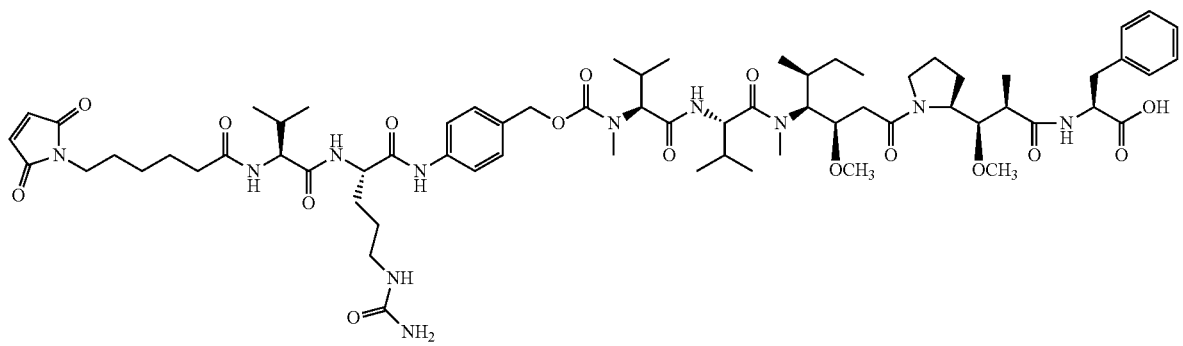

MC-val-cit-PAB-MMAF

Example 8—Preparation of hu4D5Fabv8-(LC V110C) ThioFab-BMPEO-DM1

The free cysteine on hu4D5Fabv8-(V110C) ThioFab was modified by the bis-maleimido reagent BM(PEO)3 (Pierce Chemical), leaving an unreacted maleimido group on the surface of the antibody. This was accomplished by dissolving BM(PEO)4 in a 50% ethanol/water mixture to a concentration of 10 mM and adding a tenfold molar excess of BM(PEO)3 to a solution containing hu4D5Fabv8-(V110C) ThioFab in phosphate buffered saline at a concentration of approximately 1.6 mg/ml (10 micromolar) and allowing it to react for 1 hour. Excess BM(PEO)3 was removed by gel filtration (HiTrap column, Pharmacia) in 30 mM citrate, pH 6 with 150 mM NaCl buffer. An approximate 10 fold molar excess DM1 dissolved in dimethyl acetamide (DMA) was added to the hu4D5Fabv8-(LC V110C) ThioFab-BMPEO intermediate. Dimethylformamide (DMF) may also be employed to dissolve the drug moiety reagent. The reaction mixture was allowed to react overnight before gel filtration or dialysis into PBS to remove unreacted drug. Gel filtration on 5200 columns in PBS was used to remove high molecular weight aggregates and furnish purified hu4D5Fabv8-(LC V110C) ThioFab-BMPEO-DM1.

By the same protocol, hu4D5Fabv8 (HC A121C) ThioFab-BMPEO-DM1 was prepared.

Example 9—In Vitro Cell Proliferation Assay

Efficacy of ADC were measured by a cell proliferation assay employing the following protocol (CellTiter Glo Luminiscent Cell Viability Assay, Promega Corp. Technical Bulletin TB288; Mendoza et al (2002) Cancer Res. 62:5485-5488):

1. An aliquot of 100 µl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Certain cells are seeded at 1000-2000/well (PC3 lines) or 2000-3000/well (OVCAR-3) in a 96-well plate, 50 uL/well. After one (PC3) or two (OVCAR-3) days, ADC are added in 50 µL volumes to final concentration of 9000, 3000, 1000, 333, 111, 37, 12.4, 4.1, or 1.4 ng/mL, with "no ADC" control wells receiving medium alone. Conditions are in duplicate or triplicate After 3 (PC3) or 4-5 (OVCAR-3) days, 100 µL/well Cell TiterGlo II is added (luciferase-based assay; proliferation measured by ATP levels) and cell counts are determined using a luminometer. Data are plotted as the mean of luminescence for each set of replicates, with standard deviation error bars. The protocol is a modification of the CellTiter Glo Luminiscent Cell Viability Assay (Promega):

1. Plate 1000 cells/well of PC3/Muc16, PC3/neo (in 50 µL/well) of media. Ovcar3 cells should be plated at 2000 cells/well (in 50 µL) of their media. (recipes below) Allow cells to attach overnight.
2. ADC is serially diluted 1:3 in media beginning at working concentration 18 µg/ml (this results in a final concentration of 9 µg/ml). 50 µL of diluted ADC is added to the 50 µL of cells and media already in the well.
3. Incubate 72-96 hrs (the standard is 72 hours, but watch the 0 ug/mL concentration to stop assay when the cells are 85-95% confluent).
4. Add 100 µL/well of Promega Cell Titer Glo reagent, shake 3 min. and read on luminometer Media: PC3/neo and PC3/MUC16 grow in 50/50/10% FBS/glutamine/250 µg/mL G-418 OVCAR-3 grow in RPMI/20% FBS/glutamine

Example 10—Tumor Growth Inhibition, In Vivo Efficacy in High Expressing HER2 Transgenic Explant Mice Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6xFVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.

Animals having tumors (allograft propagated from Fo5 mmtv transgenic mice) were treated with a single or multiple dose by IV injection of ADC. Tumor volume was assessed at various time points after injection.

Tumors arise readily in transgenic mice that express a mutationally activated form of neu, the rat homolog of HER2, but the HER2 that is overexpressed in human breast cancers is not mutated and tumor formation is much less robust in transgenic mice that overexpress nonmutated HER2 (Webster et al (1994) Semin. Cancer Biol. 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al (1999) J. Biol. Chem. 274: 24335-24341). Additionally, a chimeric intron was added to the 5' end, which should also enhance the level of expression as reported earlier (Neuberger and Williams (1988) Nucleic Acids Res. 16:6713; Buchman and Berg (1988) Mol. Cell. Biol. 8:4395; Brinster et al (1988) Proc. Natl. Acad. Sci. USA 85:836). The chimeric intron was derived from a Promega vector, Pci-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al (1997) Breast Cancer Res. and Treatment 45:149-158).

Example 11—Reduction/Oxidation of ThioMabs for Conjugation

Full length, cysteine engineered monoclonal antibodies (ThioMabs) expressed in CHO cells were reduced with about a 50 fold excess of TCEP (tris(2-carboxyethyl)phosphine hydrochloride; Getz et al (1999) Anal. Biochem. Vol 273:73-80; Soltec Ventures, Beverly, MA) for 3 hrs at 37° C. The reduced ThioMab (FIG. 11) was diluted and loaded onto a HiTrap S column in 10 mM sodium acetate, pH 5, and eluted with PBS containing 0.3M sodium chloride. The eluted reduced ThioMab was treated with 200 nM aqueous copper sulfate ($CuSO_4$) at room temperature, overnight. Dehydroascorbic acid (DHAA) and ambient air oxidation are also effective oxidants.

Example 12—Conjugation of ThioMabs

The reoxidized ThioMabs from Example 11, including thio-trastuzumab (HC A121C), thio-2H9 (A121C), and thio-3A5 (A121C), were combined with a 10 fold excess of drug-linker intermediate, BM(PEO)$_3$-DM1, mixed, and let stand for about an hour at room temperature to effect conjugation and form the ThioMab antibody-drug conjugates, including thio-trastuzumab (HC A121C)-BMPEO-DM1, thio-2H9 (HC A121C)-BMPEO-DM1, and thio-3A5 (HC A121C)-BMPEO-DM1. The conjugation mixture was gel filtered, or loaded and eluted through a HiTrap S column to remove excess drug-linker intermediate and other impurities.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All patents, patent applications, and references cited throughout the specification are expressly incorporated by reference in their entirety and for all purposes.

We claim:

1. An isolated cysteine engineered antibody comprising a free cysteine amino acid in the heavy chain located at position 200 or 212 by sequential numbering, or a free cysteine amino acid in the light chain located at position 155 by sequential numbering.

2. An isolated cysteine engineered antibody comprising a free cysteine amino acid, wherein the cysteine engineered antibody comprises a sequence in the heavy chain selected from
   HC-T200C with the sequence SLGTQCYICNV (SEQ ID NO: 92) and
   HC-T212C with the sequence HKPSNCKVDKK (SEQ ID NO: 95);
or a sequence in the light chain selected from
   LC-Q155C with the sequence VDNALCSGNSQ (SEQ ID NO: 135) and
   LC-T206C with the sequence LSSPVCKSFNR (SEQ ID NO: 146);
wherein the free cysteine amino acid is in the center of the sequence.

3. The cysteine engineered antibody of claim 1 wherein the cysteine engineered antibody is a monoclonal antibody.

4. The cysteine engineered antibody of claim 1 wherein the cysteine engineered antibody is an antibody fragment, wherein the fragment is a Fab, Fab', F(ab')$_2$, Fv, or scFv fragment.

5. The cysteine engineered antibody of claim 1 wherein the cysteine engineered antibody is a bispecific antibody.

* * * * *

SEQUENCE LISTING

```
<160> NUMBER OF SEQ ID NOS: 147

<210> SEQ ID NO 1
<211> LENGTH: 30
<212> TYPE: PRT
<213> ORGANISM: Artificial sequence
<220> FEATURE:
<223> OTHER INFORMATION: Exemplary albumin binding peptide sequence

<400> SEQUENCE: 1

Cys Asp Lys Thr His Thr Gly Gly Gly Ser Gln Arg Leu Met Glu Asp
1               5                   10                  15

Ile Cys Leu Pro Arg Trp Gly Cys Leu Trp Glu Asp Asp Phe
            20                  25                  30

<210> SEQ ID NO 2
<211> LENGTH: 20
<212> TYPE: PRT
<213> ORGANISM: Artificial sequence
<220> FEATURE:
<223> OTHER INFORMATION: Exemplary albumin binding peptide sequence

<400> SEQUENCE: 2

Gln Arg Leu Met Glu Asp Ile Cys Leu Pro Arg Trp Gly Cys Leu Trp
```

```
1               5                   10                  15

Glu Asp Asp Phe
            20

<210> SEQ ID NO 3
<211> LENGTH: 20
<212> TYPE: PRT
<213> ORGANISM: Artificial sequence
<220> FEATURE:
<223> OTHER INFORMATION: Exemplary albumin binding peptide sequence

<400> SEQUENCE: 3

Gln Arg Leu Ile Glu Asp Ile Cys Leu Pro Arg Trp Gly Cys Leu Trp
1               5                   10                  15

Glu Asp Asp Phe
            20

<210> SEQ ID NO 4
<211> LENGTH: 18
<212> TYPE: PRT
<213> ORGANISM: Artificial sequence
<220> FEATURE:
<223> OTHER INFORMATION: Exemplary albumin binding peptide sequence

<400> SEQUENCE: 4

Arg Leu Ile Glu Asp Ile Cys Leu Pro Arg Trp Gly Cys Leu Trp Glu
1               5                   10                  15

Asp Asp

<210> SEQ ID NO 5
<211> LENGTH: 11
<212> TYPE: PRT
<213> ORGANISM: Artificial sequence
<220> FEATURE:
<223> OTHER INFORMATION: Exemplary albumin binding peptide sequence

<400> SEQUENCE: 5

Asp Ile Cys Leu Pro Arg Trp Gly Cys Leu Trp
1               5                   10

<210> SEQ ID NO 6
<211> LENGTH: 450
<212> TYPE: PRT
<213> ORGANISM: Artificial sequence
<220> FEATURE:
<223> OTHER INFORMATION: A88C mutant heavy chain sequence (450 aa)

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Cys Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

-continued

```
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 7
<211> LENGTH: 450
<212> TYPE: PRT
<213> ORGANISM: Artificial sequence
<220> FEATURE:
<223> OTHER INFORMATION: A121C mutant heavy chain sequence (450 aa)

<400> SEQUENCE: 7

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Asn Ile Lys Asp Thr
         20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Cys Ser Lys Gly Pro Ser Val
         115                 120                 125

Phe Pro Leu Ala Pro Ser Ser Lys Ser Thr Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

```
Glu Ala Leu His Asn His Tyr Thr Gln Lys Ser Leu Ser Leu Ser Pro
            435                 440                 445

Gly Lys
    450

<210> SEQ ID NO 8
<211> LENGTH: 214
<212> TYPE: PRT
<213> ORGANISM: Artificial sequence
<220> FEATURE:
<223> OTHER INFORMATION: V110C mutant light chain sequence (214 aa)

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Cys Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 10
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 9

Trp Val Arg Gln Cys Pro Gly Lys Gly Leu
1               5                   10

<210> SEQ ID NO 10
<211> LENGTH: 10
<212> TYPE: PRT
<213> ORGANISM: Artificial sequence
<220> FEATURE:
<223> OTHER INFORMATION: Exemplary variable region heavy chain sequence
``` with a free cysteine amino acid

<400> SEQUENCE: 10

Asn Ser Leu Arg Cys Glu Asp Thr Ala Val
1               5                   10

<210> SEQ ID NO 11
<211> LENGTH: 13
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 11

Leu Val Thr Val Cys Ser Ala Ser Thr Lys Gly Pro Ser
1               5                   10

<210> SEQ ID NO 12
<211> LENGTH: 13
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 12

Leu Val Thr Val Ser Cys Ala Ser Thr Lys Gly Pro Ser
1               5                   10

<210> SEQ ID NO 13
<211> LENGTH: 13
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 13

Leu Val Thr Val Ser Ser Cys Ser Thr Lys Gly Pro Ser
1               5                   10

<210> SEQ ID NO 14
<211> LENGTH: 13
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 14

Leu Val Thr Val Ser Ser Ala Cys Thr Lys Gly Pro Ser
1               5                   10

<210> SEQ ID NO 15
<211> LENGTH: 14
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 15

His Thr Phe Pro Cys Val Leu Gln Ser Ser Gly Leu Tyr Ser
1               5                   10

<210> SEQ ID NO 16

```
<211> LENGTH: 14
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 16

His Thr Phe Pro Ala Val Leu Gln Cys Ser Gly Leu Tyr Ser
1               5                   10

<210> SEQ ID NO 17
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 17

Ser Leu Ser Ala Ser Cys Gly Asp Arg Val Thr
1               5                   10

<210> SEQ ID NO 18
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 18

Gln Lys Pro Gly Lys Cys Pro Lys Leu Leu Ile
1               5                   10

<210> SEQ ID NO 19
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 19

Glu Ile Lys Arg Thr Cys Ala Ala Pro Ser Val
1               5                   10

<210> SEQ ID NO 20
<211> LENGTH: 12
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 20

Thr Cys Ala Ala Pro Cys Val Phe Ile Phe Pro Pro
1               5                   10

<210> SEQ ID NO 21
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 21
```

```
Phe Ile Phe Pro Pro Cys Asp Glu Gln Leu Lys
1               5                   10
```

```
<210> SEQ ID NO 22
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 22

Asp Glu Gln Leu Lys Cys Gly Thr Ala Ser Val
1               5                   10
```

```
<210> SEQ ID NO 23
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 23

Phe Tyr Pro Arg Glu Cys Lys Val Gln Trp Lys
1               5                   10
```

```
<210> SEQ ID NO 24
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 24

Trp Lys Val Asp Asn Cys Leu Gln Ser Gly Asn
1               5                   10
```

```
<210> SEQ ID NO 25
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 25

Ala Leu Gln Ser Gly Cys Ser Gln Glu Ser Val
1               5                   10
```

```
<210> SEQ ID NO 26
<211> LENGTH: 11
<212> TYPE: PRT
<213> ORGANISM: Artificial sequence
<220> FEATURE:
<223> OTHER INFORMATION: Exemplary variable region light chain sequence
      with a free cysteine amino acid

<400> SEQUENCE: 26

Val Thr Glu Gln Asp Cys Lys Asp Ser Thr Tyr
1               5                   10
```

```
<210> SEQ ID NO 27
<211> LENGTH: 11
<212> TYPE: PRT
<213> ORGANISM: Artificial sequence
<220> FEATURE:
```

<223> OTHER INFORMATION: Exemplary variable region light chain sequence
      with a free cysteine amino acid

<400> SEQUENCE: 27

Gly Leu Ser Ser Pro Cys Thr Lys Ser Phe Asn
1               5                   10

<210> SEQ ID NO 28
<211> LENGTH: 450
<212> TYPE: PRT
<213> ORGANISM: Artificial sequence
<220> FEATURE:
<223> OTHER INFORMATION: A121C 2H9 mutant heavy chain sequence (450 aa)

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Trp Met His Trp Val Arg Gln Ala Pro Gly Lys Gly Leu Glu Trp Val
            35                  40                  45

Gly Phe Ile Asn Pro Ser Thr Gly Tyr Thr Asp Tyr Asn Gln Lys Phe
        50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Pro Lys Ile Pro Arg His Ala Asn Val Phe Trp Gly Gln
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu

```
                    325                 330                 335
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 29
<211> LENGTH: 25
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 29

His Glu Asp Pro Glu Cys Lys Phe Asn Trp Tyr Val Asp Gly Val Glu
1               5                   10                  15

Val His Asn Ala Lys Thr Lys Pro Arg
            20                  25

<210> SEQ ID NO 30
<211> LENGTH: 25
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 30

His Glu Asp Pro Glu Val Lys Phe Asn Trp Tyr Cys Asp Gly Val Glu
1               5                   10                  15

Val His Asn Ala Lys Thr Lys Pro Arg
            20                  25

<210> SEQ ID NO 31
<211> LENGTH: 25
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 31

His Glu Asp Pro Glu Val Lys Phe Asn Trp Tyr Val Asp Gly Cys Glu
1               5                   10                  15

Val His Asn Ala Lys Thr Lys Pro Arg
            20                  25

<210> SEQ ID NO 32
```

```
<211> LENGTH: 25
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 32

His Glu Asp Pro Glu Val Lys Phe Asn Trp Tyr Val Asp Gly Val Glu
1               5                   10                  15

Cys His Asn Ala Lys Thr Lys Pro Arg
            20                  25

<210> SEQ ID NO 33
<211> LENGTH: 25
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 33

His Glu Asp Pro Glu Val Lys Phe Asn Trp Tyr Val Asp Gly Val Glu
1               5                   10                  15

Val His Asn Cys Lys Thr Lys Pro Arg
            20                  25

<210> SEQ ID NO 34
<211> LENGTH: 11
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 34

Tyr Lys Cys Lys Val Cys Asn Lys Ala Leu Pro
1               5                   10

<210> SEQ ID NO 35
<211> LENGTH: 13
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 35

Ile Glu Lys Thr Ile Cys Lys Ala Lys Gly Gln Pro Arg
1               5                   10

<210> SEQ ID NO 36
<211> LENGTH: 13
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 36

Ile Glu Lys Thr Ile Ser Lys Cys Lys Gly Gln Pro Arg
1               5                   10

<210> SEQ ID NO 37
<211> LENGTH: 11
<212> TYPE: PRT
<213> ORGANISM: Artificial sequence
```

```
<220> FEATURE:
<223> OTHER INFORMATION: Exemplary Fc constant region heavy chain
      sequence with a free cysteine amino acid

<400> SEQUENCE: 37

Lys Gly Phe Tyr Pro Cys Asp Ile Ala Val Glu
1               5                   10

<210> SEQ ID NO 38
<211> LENGTH: 11
<212> TYPE: PRT
<213> ORGANISM: Artificial sequence
<220> FEATURE:
<223> OTHER INFORMATION: Exemplary Fc constant region heavy chain
      sequence with a free cysteine amino acid

<400> SEQUENCE: 38

Pro Pro Val Leu Asp Cys Asp Gly Ser Phe Phe
1               5                   10

<210> SEQ ID NO 39
<211> LENGTH: 446
<212> TYPE: PRT
<213> ORGANISM: Artificial sequence
<220> FEATURE:
<223> OTHER INFORMATION: A121C 3A5 mutant heavy chain sequence (446 aa)

<400> SEQUENCE: 39

Asp Val Gln Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Asn Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Tyr Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
                85                  90                  95

Ala Arg Trp Asp Gly Gly Leu Thr Tyr Trp Gly Gln Gly Thr Leu Val
            100                 105                 110

Thr Val Ser Ala Cys Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
```

```
                245                 250                 255
Glu Val Thr Cys Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 40
<211> LENGTH: 10
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 40

Asn Trp Ile Arg Gln Cys Pro Gly Asn Lys
1               5                   10

<210> SEQ ID NO 41
<211> LENGTH: 11
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 41

Leu Asn Ser Cys Thr Thr Glu Asp Thr Ala Thr
1               5                   10

<210> SEQ ID NO 42
<211> LENGTH: 21
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 42

Gly Gln Gly Thr Leu Val Thr Val Ser Ala Cys Ser Thr Lys Gly Pro
1               5                   10                  15
```

```
Ser Val Phe Pro Leu
            20

<210> SEQ ID NO 43
<211> LENGTH: 14
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 43

His Thr Phe Pro Cys Val Leu Gln Ser Ser Gly Leu Tyr Ser
1               5                   10

<210> SEQ ID NO 44
<211> LENGTH: 14
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 44

His Thr Phe Pro Ala Cys Leu Gln Ser Ser Gly Leu Tyr Ser
1               5                   10

<210> SEQ ID NO 45
<211> LENGTH: 11
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 45

Phe Leu Ser Val Ser Cys Gly Gly Arg Val Thr
1               5                   10

<210> SEQ ID NO 46
<211> LENGTH: 11
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 46

Gln Lys Pro Gly Asn Cys Pro Arg Leu Leu Ile
1               5                   10

<210> SEQ ID NO 47
<211> LENGTH: 11
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 47

Glu Ile Lys Arg Thr Cys Ala Ala Pro Ser Val
1               5                   10

<210> SEQ ID NO 48
<211> LENGTH: 11
<212> TYPE: PRT
<213> ORGANISM: Artificial sequence
```

```
<220> FEATURE:
<223> OTHER INFORMATION: Exemplary variable region heavy chain sequence
      with a free cysteine amino acid

<400> SEQUENCE: 48

Phe Tyr Pro Arg Glu Cys Lys Val Gln Trp Lys
1               5                   10

<210> SEQ ID NO 49
<211> LENGTH: 11
<212> TYPE: PRT
<213> ORGANISM: Artificial sequence
<220> FEATURE:
<223> OTHER INFORMATION: Exemplary variable region heavy chain sequence
      with a free cysteine amino acid

<400> SEQUENCE: 49

Val Thr Glu Gln Asp Cys Lys Asp Ser Thr Tyr
1               5                   10

<210> SEQ ID NO 50
<211> LENGTH: 9
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 50

Glu Val Gln Cys Val Glu Ser Gly Gly
1               5

<210> SEQ ID NO 51
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 51

Gln Leu Val Glu Ser Cys Gly Gly Leu Val Gln
1               5                   10

<210> SEQ ID NO 52
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 52

Val Glu Ser Gly Gly Cys Leu Val Gln Pro Gly
1               5                   10

<210> SEQ ID NO 53
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 53

Gly Gly Ser Leu Arg Cys Ser Cys Ala Ala Ser
1               5                   10
```

```
<210> SEQ ID NO 54
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 54

Leu Arg Leu Ser Cys Cys Ala Ser Gly Phe Asn
1               5                   10

<210> SEQ ID NO 55
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 55

Ser Cys Ala Ala Ser Cys Phe Asn Ile Lys Asp
1               5                   10

<210> SEQ ID NO 56
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 56

Cys Ala Ala Ser Gly Cys Asn Ile Lys Asp Thr
1               5                   10

<210> SEQ ID NO 57
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 57

Phe Asn Ile Lys Asp Cys Tyr Ile His Trp Val
1               5                   10

<210> SEQ ID NO 58
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 58

Ile His Trp Val Arg Cys Ala Pro Gly Lys Gly
1               5                   10

<210> SEQ ID NO 59
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant
```

```
<400> SEQUENCE: 59

Trp Val Arg Gln Ala Cys Gly Lys Gly Leu Glu
1               5                   10

<210> SEQ ID NO 60
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 60

Arg Gln Ala Pro Gly Cys Gly Leu Glu Trp Val
1               5                   10

<210> SEQ ID NO 61
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 61

Gln Ala Pro Gly Lys Cys Leu Glu Trp Val Ala
1               5                   10

<210> SEQ ID NO 62
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 62

Gly Lys Gly Leu Glu Cys Val Ala Arg Ile Tyr
1               5                   10

<210> SEQ ID NO 63
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 63

Thr Arg Tyr Ala Asp Cys Val Lys Gly Arg Phe
1               5                   10

<210> SEQ ID NO 64
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 64

Ser Val Lys Gly Arg Cys Thr Ile Ser Ala Asp
1               5                   10

<210> SEQ ID NO 65
<211> LENGTH: 11
<212> TYPE: PRT
```

```
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 65

Phe Thr Ile Ser Ala Cys Thr Ser Lys Asn Thr
1               5                   10

<210> SEQ ID NO 66
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 66

Ser Ala Asp Thr Ser Cys Asn Thr Ala Tyr Leu
1               5                   10

<210> SEQ ID NO 67
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 67

Asp Thr Ser Lys Asn Cys Ala Tyr Leu Gln Met
1               5                   10

<210> SEQ ID NO 68
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 68

Ser Lys Asn Thr Ala Cys Leu Gln Met Asn Ser
1               5                   10

<210> SEQ ID NO 69
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 69

Lys Asn Thr Ala Tyr Cys Gln Met Asn Ser Leu
1               5                   10

<210> SEQ ID NO 70
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 70

Asn Thr Ala Tyr Leu Cys Met Asn Ser Leu Arg
1               5                   10
```

<210> SEQ ID NO 71
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 71

Leu Gln Met Asn Ser Cys Arg Ala Glu Asp Thr
1               5                   10

<210> SEQ ID NO 72
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 72

Met Asn Ser Leu Arg Cys Glu Asp Thr Ala Val
1               5                   10

<210> SEQ ID NO 73
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 73

Ser Leu Arg Ala Glu Cys Thr Ala Val Tyr Tyr
1               5                   10

<210> SEQ ID NO 74
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 74

Ala Glu Asp Thr Ala Cys Tyr Tyr Cys Ser Arg
1               5                   10

<210> SEQ ID NO 75
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 75

Glu Asp Thr Ala Val Cys Tyr Cys Ser Arg Trp
1               5                   10

<210> SEQ ID NO 76
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 76

Val Tyr Tyr Cys Ser Cys Trp Gly Gly Asp Gly
1               5                   10

<210> SEQ ID NO 77
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 77

Tyr Cys Ser Arg Trp Cys Gly Asp Gly Phe Tyr
1               5                   10

<210> SEQ ID NO 78
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 78

Gly Phe Tyr Ala Met Cys Tyr Trp Gly Gln Gly
1               5                   10

<210> SEQ ID NO 79
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 79

Asp Tyr Trp Gly Gln Cys Thr Leu Val Thr Val
1               5                   10

<210> SEQ ID NO 80
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 80

Gln Gly Thr Leu Val Cys Val Ser Ser Ala Ser
1               5                   10

<210> SEQ ID NO 81
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 81

Val Thr Val Ser Ser Cys Ser Thr Lys Gly Pro
1               5                   10

<210> SEQ ID NO 82
<211> LENGTH: 11

```
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 82

Ser Ala Ser Thr Lys Cys Pro Ser Val Phe Pro
1               5                   10

<210> SEQ ID NO 83
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 83

Lys Ser Thr Ser Gly Cys Thr Ala Ala Leu Gly
1               5                   10

<210> SEQ ID NO 84
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 84

Val Lys Asp Tyr Phe Cys Glu Pro Val Thr Val
1               5                   10

<210> SEQ ID NO 85
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 85

Val Thr Val Ser Trp Cys Ser Gly Ala Leu Thr
1               5                   10

<210> SEQ ID NO 86
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 86

Thr Val Ser Trp Asn Cys Gly Ala Leu Thr Ser
1               5                   10

<210> SEQ ID NO 87
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 87

Val Ser Trp Asn Ser Cys Ala Leu Thr Ser Gly
```

-continued

```
<210> SEQ ID NO 88
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 88

Ser Gly Ala Leu Thr Cys Gly Val His Thr Phe
1               5                   10

<210> SEQ ID NO 89
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 89

Ser Gly Val His Thr Cys Pro Ala Val Leu Gln
1               5                   10

<210> SEQ ID NO 90
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 90

Leu Ser Ser Val Val Cys Val Pro Ser Ser Ser
1               5                   10

<210> SEQ ID NO 91
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 91

Val Thr Val Pro Ser Cys Ser Leu Gly Thr Gln
1               5                   10

<210> SEQ ID NO 92
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 92

Ser Leu Gly Thr Gln Cys Tyr Ile Cys Asn Val
1               5                   10

<210> SEQ ID NO 93
<211> LENGTH: 11
<212> TYPE: PRT
<213> ORGANISM: Artificial sequence
<220> FEATURE:
<223> OTHER INFORMATION: Efficient binding, thiol-reactive heavy chain
``` hu4D5Fabv8 mutant

<400> SEQUENCE: 93

Thr Tyr Ile Cys Asn Cys Asn His Lys Pro Ser
1               5                   10

<210> SEQ ID NO 94
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 94

Asn His Lys Pro Ser Cys Thr Lys Val Asp Lys
1               5                   10

<210> SEQ ID NO 95
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 95

His Lys Pro Ser Asn Cys Lys Val Asp Lys Lys
1               5                   10

<210> SEQ ID NO 96
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 96

Pro Ser Asn Thr Lys Cys Asp Lys Lys Val Glu
1               5                   10

<210> SEQ ID NO 97
<211> LENGTH: 11
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 97

Thr Lys Val Asp Lys Cys Val Glu Pro Lys Ser
1               5                   10

<210> SEQ ID NO 98
<211> LENGTH: 7
<212> TYPE: PRT
<213> ORGANISM: Artificial sequence
<220> FEATURE:
<223> OTHER INFORMATION: Efficient binding, thiol-reactive heavy chain
      hu4D5Fabv8 mutant

<400> SEQUENCE: 98

Lys Ser Cys Asp Lys Cys His
1               5

<210> SEQ ID NO 99

```
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 99

Met Thr Gln Ser Pro Cys Ser Leu Ser Ala Ser
1               5                   10

<210> SEQ ID NO 100
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 100

Gly Lys Ala Pro Lys Cys Leu Ile Tyr Ser Ala
1               5                   10

<210> SEQ ID NO 101
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 101

Pro Lys Leu Leu Ile Cys Ser Ala Ser Phe Leu
1               5                   10

<210> SEQ ID NO 102
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 102

Ile Tyr Ser Ala Ser Cys Leu Tyr Ser Gly Val
1               5                   10

<210> SEQ ID NO 103
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 103

Ser Gly Thr Asp Phe Cys Leu Thr Ile Ser Ser
1               5                   10

<210> SEQ ID NO 104
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 104
```

```
Gly Thr Asp Phe Thr Cys Thr Ile Ser Ser Leu
1               5                   10
```

<210> SEQ ID NO 105
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 105

```
Thr Asp Phe Thr Leu Cys Ile Ser Ser Leu Gln
1               5                   10
```

<210> SEQ ID NO 106
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 106

```
Asp Phe Thr Leu Thr Cys Ser Ser Leu Gln Pro
1               5                   10
```

<210> SEQ ID NO 107
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 107

```
Thr Leu Thr Ile Ser Cys Leu Gln Pro Glu Asp
1               5                   10
```

<210> SEQ ID NO 108
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 108

```
Thr Ile Ser Ser Leu Cys Pro Glu Asp Phe Ala
1               5                   10
```

<210> SEQ ID NO 109
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 109

```
Ile Ser Ser Leu Gln Cys Glu Asp Phe Ala Thr
1               5                   10
```

<210> SEQ ID NO 110
<211> LENGTH: 11
<212> TYPE: PRT
<213> ORGANISM: Artificial sequence
<220> FEATURE:

<223> OTHER INFORMATION: Efficient binding, thiol-reactive light chain
      hu4D5Fabv8 mutant

<400> SEQUENCE: 110

Tyr Cys Gln Gln His Cys Thr Thr Pro Pro Thr
1               5                   10

<210> SEQ ID NO 111
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 111

Gln His Tyr Thr Thr Cys Pro Thr Phe Gly Gln
1               5                   10

<210> SEQ ID NO 112
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 112

Thr Pro Pro Thr Phe Cys Gln Gly Thr Lys Val
1               5                   10

<210> SEQ ID NO 113
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 113

Pro Thr Phe Gly Gln Cys Thr Lys Val Glu Ile
1               5                   10

<210> SEQ ID NO 114
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 114

Phe Gly Gln Gly Thr Cys Val Glu Ile Lys Arg
1               5                   10

<210> SEQ ID NO 115
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 115

Gln Gly Thr Lys Val Cys Ile Lys Arg Thr Val
1               5                   10

```
<210> SEQ ID NO 116
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 116

Glu Ile Lys Arg Thr Cys Ala Ala Pro Ser Val
1               5                   10

<210> SEQ ID NO 117
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 117

Lys Arg Thr Val Ala Cys Pro Ser Val Phe Ile
1               5                   10

<210> SEQ ID NO 118
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 118

Thr Val Ala Ala Pro Cys Val Phe Ile Phe Pro
1               5                   10

<210> SEQ ID NO 119
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 119

Ala Ala Pro Ser Val Cys Ile Phe Pro Pro Ser
1               5                   10

<210> SEQ ID NO 120
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 120

Pro Ser Val Phe Ile Cys Pro Pro Ser Asp Glu
1               5                   10

<210> SEQ ID NO 121
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 121
```

```
Phe Ile Phe Pro Pro Cys Asp Glu Gln Leu Lys
1               5                   10

<210> SEQ ID NO 122
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 122

Pro Ser Asp Glu Gln Cys Lys Ser Gly Thr Ala
1               5                   10

<210> SEQ ID NO 123
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 123

Asp Glu Gln Leu Lys Cys Gly Thr Ala Ser Val
1               5                   10

<210> SEQ ID NO 124
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 124

Gln Leu Lys Ser Gly Cys Ala Ser Val Val Cys
1               5                   10

<210> SEQ ID NO 125
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 125

Leu Lys Ser Gly Thr Cys Ser Val Val Cys Leu
1               5                   10

<210> SEQ ID NO 126
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 126

Lys Ser Gly Thr Ala Cys Val Val Cys Leu Leu
1               5                   10

<210> SEQ ID NO 127
<211> LENGTH: 11
<212> TYPE: PRT
<213> ORGANISM: Artificial sequence
```

```
<220> FEATURE:
<223> OTHER INFORMATION: Efficient binding, thiol-reactive light chain
      hu4D5Fabv8 mutant

<400> SEQUENCE: 127

Val Val Cys Leu Leu Cys Asn Phe Tyr Pro Arg
1               5                   10

<210> SEQ ID NO 128
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 128

Val Cys Leu Leu Asn Cys Phe Tyr Pro Arg Glu
1               5                   10

<210> SEQ ID NO 129
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 129

Leu Leu Asn Asn Phe Cys Pro Arg Glu Ala Lys
1               5                   10

<210> SEQ ID NO 130
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 130

Asn Asn Phe Tyr Pro Cys Glu Ala Lys Val Gln
1               5                   10

<210> SEQ ID NO 131
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 131

Phe Tyr Pro Arg Glu Cys Lys Val Gln Trp Lys
1               5                   10

<210> SEQ ID NO 132
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 132

Arg Glu Ala Lys Val Cys Trp Lys Val Asp Asn
1               5                   10
```

<210> SEQ ID NO 133
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 133

Ala Lys Val Gln Trp Cys Val Asp Asn Ala Leu
1               5                   10

<210> SEQ ID NO 134
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 134

Val Gln Trp Lys Val Cys Asn Ala Leu Gln Ser
1               5                   10

<210> SEQ ID NO 135
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 135

Val Asp Asn Ala Leu Cys Ser Gly Asn Ser Gln
1               5                   10

<210> SEQ ID NO 136
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 136

Gln Ser Gly Asn Ser Cys Glu Ser Val Thr Glu
1               5                   10

<210> SEQ ID NO 137
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 137

Leu Thr Leu Ser Lys Cys Asp Tyr Glu Lys His
1               5                   10

<210> SEQ ID NO 138
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

```
<400> SEQUENCE: 138

Thr Leu Ser Lys Ala Cys Tyr Glu Lys His Lys
1               5                   10

<210> SEQ ID NO 139
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 139

Lys Ala Asp Tyr Glu Cys His Lys Val Tyr Ala
1               5                   10

<210> SEQ ID NO 140
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 140

Tyr Ala Cys Glu Val Cys His Gln Gly Leu Ser
1               5                   10

<210> SEQ ID NO 141
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 141

Glu Val Thr His Gln Cys Leu Ser Ser Pro Val
1               5                   10

<210> SEQ ID NO 142
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 142

Val Thr His Gln Gly Cys Ser Ser Pro Val Thr
1               5                   10

<210> SEQ ID NO 143
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 143

His Gln Gly Leu Ser Cys Pro Val Thr Lys Ser
1               5                   10

<210> SEQ ID NO 144
<211> LENGTH: 11
<212> TYPE: PRT
```

```
<213> ORGANISM: Artificial sequence
<220> FEATURE:
<223> OTHER INFORMATION: Efficient binding, thiol-reactive light chain
      hu4D5Fabv8 mutant

<400> SEQUENCE: 144

Gln Gly Leu Ser Ser Cys Val Thr Lys Ser Phe
1               5                   10

<210> SEQ ID NO 145
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 145

Gly Leu Ser Ser Pro Cys Thr Lys Ser Phe Asn
1               5                   10

<210> SEQ ID NO 146
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 146

Leu Ser Ser Pro Val Cys Lys Ser Phe Asn Arg
1               5                   10

<210> SEQ ID NO 147
<211> LENGTH: 11
<212> TYPE: PRT
<213> ORGANISM: Artificial sequence
<220> FEATURE:
<223> OTHER INFORMATION: Efficient binding, thiol-reactive light chain
      hu4D5Fabv8 mutant

<400> SEQUENCE: 147

Ser Ser Pro Val Thr Cys Ser Phe Asn Arg Gly
1               5                   10
```